US011198878B2

United States Patent
Hardee et al.

(10) Patent No.: US 11,198,878 B2
(45) Date of Patent: *Dec. 14, 2021

(54) HIGH-EFFICIENCY TRANSFECTION OF BIOLOGICAL CELLS USING SONOPORATION

(71) Applicant: Labcyte Inc., San Jose, CA (US)

(72) Inventors: Jennifer M. Hardee, San Jose, CA (US); Richard N. Ellson, San Jose, CA (US); Richard G. Stearns, San Jose, CA (US); Babur Hadimioglu, San Jose, CA (US); Joseph D. Olechno, San Jose, CA (US); Marsha N. Blauwkamp, San Jose, CA (US)

(73) Assignee: LABCYTE INC., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/006,675

(22) Filed: Aug. 28, 2020

(65) Prior Publication Data

US 2020/0392515 A1    Dec. 17, 2020

Related U.S. Application Data

(62) Division of application No. 15/706,524, filed on Sep. 15, 2017, now Pat. No. 10,787,670.

(60) Provisional application No. 62/395,363, filed on Sep. 15, 2016, provisional application No. 62/439,458, filed on Dec. 27, 2016.

(51) Int. Cl.
| | | |
|---|---|---|
| *C07H 21/04* | (2006.01) | |
| *C12N 15/64* | (2006.01) | |
| *C12N 15/87* | (2006.01) | |
| *A61N 7/00* | (2006.01) | |
| *C12N 9/22* | (2006.01) | |
| *C12N 13/00* | (2006.01) | |
| *C12N 15/11* | (2006.01) | |

(52) U.S. Cl.
CPC .............. *C12N 15/64* (2013.01); *A61N 7/00* (2013.01); *C12N 9/22* (2013.01); *C12N 13/00* (2013.01); *C12N 15/11* (2013.01); *C12N 15/87* (2013.01); *A61N 2007/0039* (2013.01); *A61N 2007/0073* (2013.01); *C12N 2310/20* (2017.05)

(58) Field of Classification Search
None
See application file for complete search history.

(56) References Cited

U.S. PATENT DOCUMENTS

| | | |
|---|---|---|
| 6,666,541 B2 | 12/2003 | Ellson et al. |
| 7,270,986 B2 | 9/2007 | Mutz et al. |
| 8,771,945 B1 | 7/2014 | Zhang |
| 2001/0053884 A1 | 12/2001 | Kreig et al. |
| 2010/0255573 A1 | 10/2010 | Bond et al. |
| 2015/0219636 A1 | 8/2015 | Rychak et al. |

FOREIGN PATENT DOCUMENTS

| | | |
|---|---|---|
| WO | 2006105251 A2 | 10/2006 |
| WO | 2015110955 A1 | 7/2015 |

OTHER PUBLICATIONS

"Annex to Form PCT/ISA/206 Communication Relating to the Results of the Partial International Search and Provisional Opinion Accompanying the Partial Search Result, PCT/US2017/051909", dated Nov. 24, 2017, 16 pages.
"International Search Report and Written Opinion PCT/US2017/051909", dated Apr. 9, 2018, 23 pages.
Delalande, Anthony, et al., "Sonoporation: Mechanistic insights and ongoing challenges for gene transfer", Gene 38471, 2013, 9 pages.
Fan, et al., "Spatiotemporally Controlled Single Cell Sonoporation", Proc. Natl. Acad. Sci. U.S.A., 109(41), 2012, pp. 16486-16491.
Forbes, et al., "Examination of Inertial Cavitation of Optison in Producing Sonoporation of Chinese Hamster Ovary Cells", Ultrasound in Med. & Biol. 34(12), 2008, pp. 2009-2018.
Forbes, Monica Mary, "The Role of Ultrasound Contrast Agents in Producing Sonoporation", Doctoral dissertation, University of Illinois at Urbana-Champaign, 2009, 166 pages.
Mestas, J.L., "Development of a confocal ultrasound device using an inertial cavitation control for transfection", Journal of Physics: Conference Series, Institute of Physics Publishing, Bristol, GB, vol. 656, No. 1, Dec. 3, 2015, 4 pages.
Yong, et al., "Microbubble-Mediated Sonoporation for Highly Efficient Transfection of Recalcitrant Human B-Cell Lines", Biotechnol. J. 9, 2014, pp. 1081-1087.

*Primary Examiner* — Kimberly Chong
(74) *Attorney, Agent, or Firm* — Dianne E. Reed; VLP Law Group, LLP

(57) ABSTRACT

A method is provided for achieving transfection of host cells using sonoporation. An acoustic radiation generator is positioned in acoustic coupling relationship with respect to a reservoir containing host cells to be transfected, exogenous material to be incorporated into the host cells, and a cell-compatible fluid medium. The acoustic radiation generator is activated to generate acoustic radiation and direct the acoustic radiation into the reservoir in a manner effective to enable transfection of the host cells with the exogenous material.

16 Claims, 14 Drawing Sheets

HIGH-EFFICIENCY TRANSFECTION OF BIOLOGICAL CELLS USING SONOPORATION

CROSS-REFERENCE TO EARLIER APPLICATIONS

This application is a divisional of U.S. patent application Ser. No. 15/706,524, filed Sep. 15, 2017, which claims priority under 35 USC 119(e)(1) to provisional U.S. Patent Application Ser. No. 62/439,458, filed Dec. 27, 2016, and to provisional U.S. Patent Application Ser. No. 62/395,363, filed Sep. 15, 2016, the disclosures of which are incorporated by reference herein.

TECHNICAL FIELD

The present invention relates generally to biotechnology, and more particularly relates to methods and systems for the efficient transfection of biological cells. The invention finds utility in the fields of biochemistry and medicine, including cellular research and drug discovery.

BACKGROUND

Transfection refers to the incorporation of foreign material into host cells, either bacterial or mammalian. In the realm of biotechnology, transfection has become a critically important tool used to introduce foreign DNA or RNA into cells in order to produce genetically modified cells. Transfection may be either stable or transient. In stable transfection, the introduced genetic material is delivered to the host cell nucleus by passage through the cell and nuclear membranes, and becomes integrated into the host genome; every daughter cell has the added material. In transient transfection (also referred to as "transformation"), by contrast, the nucleic acid is inserted into the host cell but does not become integrated into its genome. As a result, the foreign genetic material is expressed temporarily but does not pass to future generations of the transfected cell. Accordingly, it will be appreciated that stable transfection is necessary for large-scale protein production, gene therapy, drug discovery, compound screening, and extended research. The development of stable cell lines, however, is complex, time- and labor-consuming, and costly.

There are various methods of introducing foreign genetic material into a eukaryotic host cell, including biologically, chemically, and physically mediated techniques. The most commonly used transfection method in research is biological, and involves the use of a virus as carrier. Adenoviral, lentiviral, and oncoretroviral vectors have been used extensively for gene delivery in mammalian cell culture and in vivo. Virus-mediated transfection, or viral "transduction," is efficient and relatively straightforward to use, even with cell types that are difficult to transfect. There are significant drawbacks, however, including the immunogenicity and cytotoxicity of the selected virus as well as the difficulty and time involved in producing viral vectors. Lentiviral vectors, for instance, are also biohazardous to the user and require Biosafety Level 2 (BSL-2, as established by the U.S. Centers for Disease Control and Prevention) or Enhanced BSL-2 (BSL-2+) working conditions.

Chemical transfection methods are widely used, and they were the first to be used to introduce foreign genes into mammalian host cells. Chemical methods commonly used include, without limitation, the following: calcium phosphate combined with a buffered saline/phosphate solution; cationic polymers such as a conjugate of diethylethanolamine and dextran (or "DEAE-dextran") or polyethyleneimine; cationic lipid formulations such as that commercially available under the tradename Lipofectamine® (additional cationic lipid formulations are described in the pertinent texts and literature, e.g., by Felgner et al. (1994) *J. Biol. Chem.* 269(4):2550-61); and activated dendrimers, such as polyamidoamine dendrimers (see Hudde et al. (1999) *Gene Therapy* 6(5):939-943). Chemical transfection efficiency varies depending on cell type, genetic material/chemical transfection agent ratio, solution pH, and other conditions. While chemical transfection methods are not associated with the potential immunogenicity and cytotoxicity of viral transfection agents, they generally exhibit poor transfection efficiency. Furthermore, many of the aforementioned chemical transfection reagents can be used with only a very small number of cell lines, those that are robust and not particularly sensitive, e.g., HeLa or HEK-293 cells.

Physical transfection methods are more recent than either viral or chemical transfection, and include techniques such as electroporation, laser-based transfection, biolistic particle delivery, cell squeezing, and direct micro-injection. While these methods have been established to achieve transfection, there are numerous associated problems, including the potential for extensive physical damage to samples.

In order to overcome some of the problems encountered with the aforementioned methods, there has been some effort put into using the technique of "sonoporation" to achieve transfection. Sonoporation involves the use of ultrasound, or acoustic energy, to induce a transient change in cell membrane permeability sufficient to allow the uptake of macromolecules by a host cell, where those macromolecules would otherwise not pass through the cell membrane. The work done to date in this area has focused on the use of an ultrasound contrast agent (UCA). Most UCAs are microbubbles filled with a buoyant gas, and are designed for use in medical ultrasound testing to increase acoustic reflectivity via backscattering. It has been proposed that UCAs be used in sonoporation by undergoing cavitation in the proximity of a host cell, such that the UCA first expands, but then rapidly contracts or collapses, generating microstreams or shock waves that apply shear stress to cell membranes, temporarily or permanently rupturing those membranes. More recently, it has been suggested that sonoporation can occur using UCAs with acoustic energies below that which would cause cavitation. See, e.g., Forbes et al. (2008) *Ultrasound in Med. & Biol.* 34(12):2009-2018. The process has not been implemented on a larger scale, however, for a variety of reasons, including the fact that in a liquid medium, UCAs will rise to the liquid surface, while the host cells will gravitate downward. This is problematic, since transfection via sonoporation requires that the buoyant microbubbles and the host cells be adjacent when acoustic energy is applied. Another issue is efficiency: to date, there has been no report of a sonoporation-based transfection method in which the number of successfully transfected host cells is maximized while cell death is minimized. Furthermore, like other transfection techniques, sonoporation, to date, has been ineffective in transfecting for cells that are difficult to transfect, e.g., primary cells, particularly stem cells.

An ideal transfection method would do the following:

Maximize the fraction of host cells that are transfected while minimizing cell death;

Allow for the successful transfection of a variety of cell types, including cells that are typically resistant to transfection;

Enable transfection of non-mammalian cells as well as mammalian cells;

Enable transfection of confluent as well as non-confluent cells;

Allow for transfection of cells with nucleic acids such as DNA, RNA, small interfering RNA (siRNA/RNAi), micro RNA (miRNA), and DNA plasmids;

Allow for transfection of cells with other types of exogenous material, including proteins and small molecules;

Work with nucleic acid sequences and associated proteins selected for modification of target cell function and machinery for execution of gene expression, including (a) ribonucleoproteins (RNPs) composed of Cas9 protein and guide RNA and (b) CRISPR plasmid with associated promoters;

Involve straightforward implementation without requiring an inordinate amount of time or labor; and As a result of speed and ease of implementation, be adaptable to use in high-throughput transfection.

SUMMARY OF THE INVENTION

Accordingly, the present invention addresses the above-discussed need in the art and provides a sonoporation-based method for transfecting host cells.

In one embodiment, the invention provides an acoustic method for transfecting cells, the method comprising:

(a) providing a system that comprises (i) at least two reservoirs each containing host cells and exogenous material to be introduced into the host cells, and (ii) an acoustic radiation generator to generate and direct acoustic radiation;

(b) acoustically coupling the acoustic radiation generator to a first of the reservoirs without simultaneously acoustically coupling the acoustic radiation generator to any other of the reservoirs;

(c) activating the acoustic radiation generator to generate and direct acoustic radiation into the first reservoir in a manner that induces sonoporation of the host cells, thereby facilitating introduction of the exogenous material into the sonoporated host cells;

(d) acoustically decoupling the acoustic radiation generator from the first reservoir;

(e) acoustically coupling the acoustic radiation generator to a second of the reservoirs without simultaneously acoustically coupling the acoustic radiation generator to any other of the reservoirs; and (f) repeating step (c) with respect to the second reservoir.

In one aspect of this embodiment, the at least two reservoirs are contained within a plurality of reservoirs, and the method further includes (g) acoustically decoupling the acoustic radiation generator from the second reservoir and thereafter repeating steps (b) through (g) with respect to additional reservoirs. The reservoirs may be contained within an integrated multiple reservoir unit such as a microwell plate, such as a 96-well plate, a 384-well plate, a 1536-well plate, or the like. The acoustic radiation directed into the reservoir, in one aspect of this embodiment, is focused acoustic radiation.

In another aspect of this embodiment, the method is carried out within the context of a high-throughput transfection system, in which host cells in each of a plurality of multiple reservoirs are rapidly sonoporated in succession. This may mean a reservoir-to-reservoir transition time of at most about 0.5 seconds, 0.1 seconds, or 0.001 seconds. In a related aspect, the volume of fluid medium in each reservoir may be in the range of about 0.5 µL to about 500 µL.

In another aspect of this embodiment, the manner for inducing sonoporation includes a means for imparting the acoustic radiation generated to the host cells, generally a transfection excitation material that comprises a plurality of acoustically activatable moieties within the fluid medium, such as acoustically activatable localized fluid volumes. The localized fluid volumes may be gas-filled microbubbles, which may be conjugated to the host cells to facilitate transfer of acoustic energy from the irradiated microbubbles to the host cells.

In another embodiment, a method is provided for transfecting host cells, comprising:

(a) preparing a microbubble composition by suspending, in a fluid medium compatible with the host cells, a plurality of gas-filled microbubbles surface-functionalized with a first binding moiety;

(b) conjugating the microbubbles to antibodies specific for the host cell type and functionalized with a second binding moiety that links to the first binding moiety, by mixing the microbubbles with the antibodies in the fluid medium, thereby creating microbubble-antibody conjugates;

(c) preparing loaded microbubble-antibody conjugates by mixing the microbubble-antibody conjugates with an exogenous material to be transfected into the host cells;

(d) optionally diluting the loaded microbubble-antibody conjugates with a host cell-compatible fluid medium that provides a dilution having a loaded microbubble-antibody conjugate concentration effective to optimize transfection efficiency;

(e) contacting host cells in a reservoir with the dilution;

(f) sonoporating the host cell-dilution mixture provided in (e) by irradiating the reservoir with acoustic radiation under conditions that cause the microbubbles to resonate at a frequency within about 15% of their average resonance frequency or within about 15% of a harmonic of their average resonance frequency.

In another embodiment, the invention provides an acoustic method for transfecting cells that comprises: acoustically coupling an acoustic radiation generator to a reservoir that contains host cells, exogenous material to be transfected into the host cells, and a fluid medium; and activating the acoustic radiation generator to generate acoustic radiation and direct the acoustic radiation into the reservoir in a manner that induces sonoporation of the host cells without resulting in a temperature increase in the fluid medium of greater than about 10° C.

In another embodiment, the invention provides an acoustic method for transfecting cells that comprises: acoustically coupling an acoustic radiation generator to a selected reservoir contained within an integral multiple reservoir unit comprising at least 1536 reservoirs, the selected reservoir containing host cells, exogenous material to be transfected into the host cells, and a fluid medium; and activating the acoustic radiation generator to generate acoustic radiation and direct the acoustic radiation into the reservoir in a manner that induces sonoporation of the host cells, thereby facilitating incorporation of the exogenous material into the sonoporated host cells.

In another embodiment, the invention provides an acoustic method for transfecting cells that comprises: acoustically coupling an acoustic radiation generator to a reservoir that contains host cells, exogenous material to be transfected into the host cells, a fluid medium, and a transfection excitation material comprised of a plurality of acoustically activatable localized fluid volumes; and activating the acoustic radiation generator to generate acoustic radiation and direct the acoustic radiation into the reservoir in a manner that acoustically activates the localized fluid volumes so that they vibrate at a frequency that is within about 15% of the average resonance frequency of the localized fluid volumes or within about 15% of a harmonic of the average resonance frequency of the localized fluid volumes, thereby facilitating incorporation of the exogenous material into host cells in the proximity of the acoustically activated localized fluid volumes.

In another embodiment, the invention provides an acoustic method for transfecting cells that comprises: acoustically coupling an acoustic radiation generator to a reservoir that contains host cells, exogenous material to be transfected into the host cells, a fluid medium, and a transfection excitation material comprised of a plurality of acoustically activatable localized fluid volumes having a size distribution; and activating the acoustic radiation generator to generate acoustic radiation and direct the acoustic radiation into the reservoir in a manner that acoustically activates the localized fluid volumes having a size within about 15% of a selected size, thereby facilitating incorporation of the exogenous material into host cells in the proximity of the acoustically activated localized fluid volumes.

In a related embodiment, the invention provides an acoustic method for transfecting cells that comprises: (a) acoustically coupling an acoustic radiation generator to a reservoir that contains host cells, exogenous material to be transfected into the host cells, a fluid medium, and a transfection excitation material comprised of a plurality of acoustically activatable localized fluid volumes having a multimodal size distribution; (b) activating the acoustic radiation generator to generate acoustic radiation and direct the acoustic radiation into the reservoir in a manner that acoustically activates localized fluid volumes having a size that is within about 15% of a first modal peak, whereby the acoustically activated localized fluid volumes transfer acoustic energy to nearby host cells; (c) repeating step (b) to acoustically activate localized fluid volumes having a size that is within about 15% of a second modal peak; and (d) optionally repeating step (b) to acoustically activate localized fluid volumes having a size that is within about 15% of one or more additional modal peaks.

In an additional embodiment, the invention provides an acoustic method for transfecting cells that comprises: acoustically coupling an acoustic radiation generator to a reservoir containing host cells, exogenous material to be transfected into the host cells, a fluid medium, and a transfection excitation material comprised of a plurality of acoustically activatable localized fluid volumes having a size distribution; and activating the acoustic radiation generator to generate acoustic radiation having a selected frequency content and direct the acoustic radiation generated into the reservoir in a manner that induces sonoporation of the host cells, wherein the frequency content of the acoustic radiation generated is selected to correlate with the size distribution of the acoustically activatable localized fluid volumes.

In a related embodiment, the invention provides an acoustic method for transfecting cells that comprises: acoustically coupling an acoustic radiation generator to a reservoir containing host cells, exogenous material to be transfected into the host cells, a fluid medium, and a transfection excitation material comprised of a plurality of acoustically activatable localized fluid volumes having a spatial distribution within the reservoir; and activating the acoustic radiation generator to generate acoustic radiation having a selected frequency content and direct the acoustic radiation generated into the reservoir in a manner that induces sonoporation of the host cells, thereby facilitating incorporation of the exogenous material into the sonoporated host cells, wherein the frequency content of the acoustic radiation generated is selected to correlate with the spatial distribution of the acoustically activatable localized fluid volumes.

In another embodiment, sonoporation is conducted using two transducers operating in concert (preferably but not necessarily simultaneously) but at different frequencies, wherein one of the transducers is an annular transducer is operably mounted around and enclosing a standard transducer. In this embodiment, the annular transducer and the standard transducer will generally operate at different frequencies. In one aspect of this embodiment, the annular transducer may operate at a frequency selected to bring about sonoporation, while the standard transducer can be operated at a frequency effective to result in acoustic ejection of sonoporated cells, e.g., into a reservoir, onto a substrate, or to an analytical instrument for analysis. In another aspect of this embodiment, one of the two transducers primarily functions to supply the acoustic energy for sonoporation and the other transducer delivers acoustic energy to change the relative position of the microbubbles with respect to the host cells when microbubble-cell conjugation is not used.

In another embodiment, sonoporation is carried out by irradiating with multiple acoustic tonebursts in succession, each having a different acoustic frequency effective to sonoporate differently sized microbubbles. The acoustic frequency of each of the multiple acoustic tonebursts is typically in the range of about 1.5 MHz to about 5.0 MHz, more usually in the range of about 2.0 MHz to about 2.5 MHz.

In a further embodiment, an acoustic method for transfecting cells is provided that comprises: acoustically coupling an acoustic radiation generator to a selected reservoir containing host cells, exogenous material to be transfected into the host cells, a fluid medium, and a transfection excitation material comprising a plurality of acoustically activatable localized fluid volumes; and activating the acoustic radiation generator to generate acoustic radiation and direct the acoustic radiation into the reservoir in a manner that acoustically activates the localized fluid volumes, thereby facilitating incorporation of the exogenous material into host cells in the proximity of the acoustically activated localized fluid volumes, wherein the acoustic radiation generated is at an acoustic sonoporation pressure selected to ensure that at least 50% of the localized fluid volumes remain intact after irradiation. In one aspect of this embodiment, the acoustic sonoporation is in the range of about 50% to about 90% of the minimum acoustic pressure that would result in cavitation of the localized fluid volumes.

DETAILED DESCRIPTION OF THE INVENTION

Figure 1:
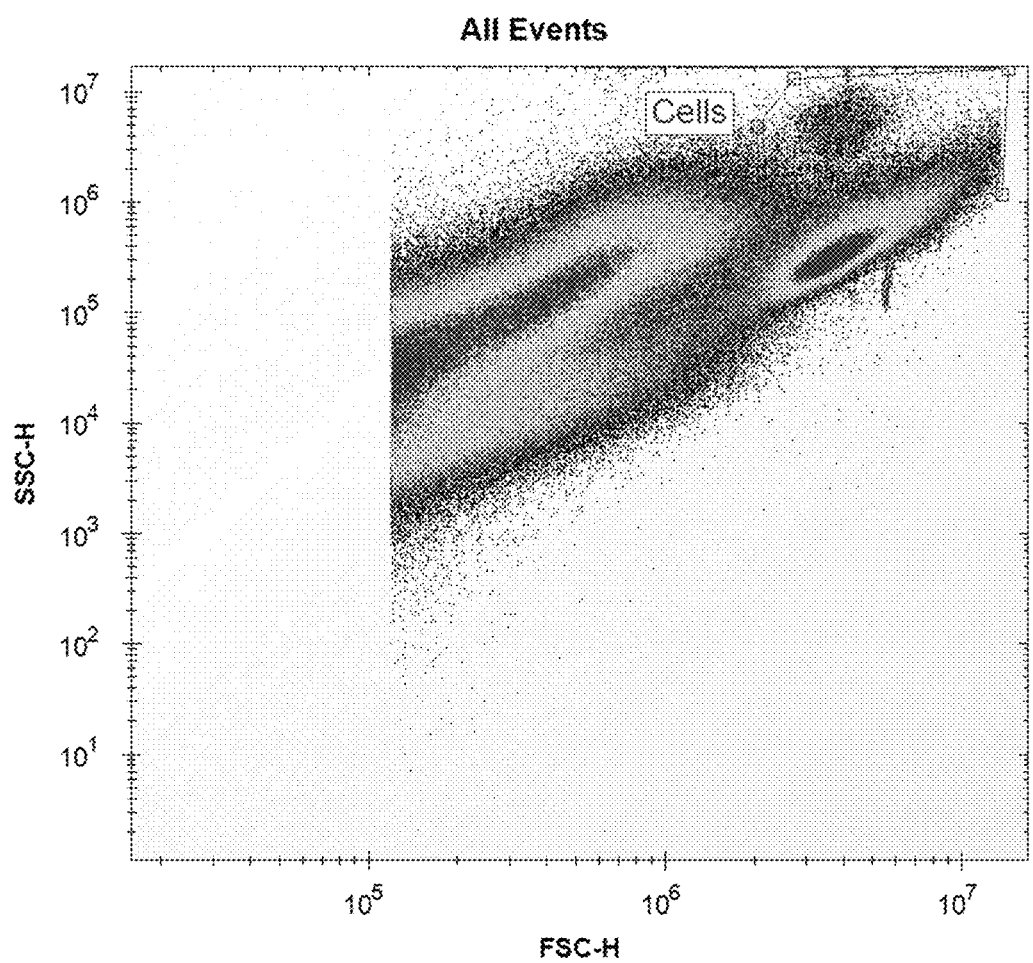
FIG. 1 provides a plot of forward versus side scatter height in the FACS analysis described in Example 4.

Unless defined otherwise, all technical and scientific terms used herein have the meaning commonly understood by one of ordinary skill in the art to which the invention pertains. Specific terminology of particular importance to the description of the present invention is defined below.

In this specification and the appended claims, the singular forms "a," "an" and "the" include plural referents unless the context clearly dictates otherwise. Thus, for example, "a component" refers not only to a single component but also to a combination of two or more different components, and the like.

The terms "acoustic radiation" and "acoustic energy" are used interchangeably herein and refer to the emission and propagation of energy in the form of sound waves. As with other waveforms, acoustic radiation may be focused using a focusing means, as discussed below.

The terms "focusing means" and "acoustic focusing means" refer to a means for causing acoustic waves to converge at a focal point, either by a device separate from the acoustic energy source that acts like a lens, or by the spatial arrangement of acoustic energy sources to effect convergence of acoustic energy at a focal point by constructive and destructive interference. A focusing means may be as simple as a solid member having a curved surface, or it may include complex structures such as those found in Fresnel lenses, which employ diffraction in order to direct acoustic radiation. Suitable focusing means also include phased array methods as are known in the art and described, for example, in U.S. Pat. No. 5,798,779 to Nakayasu et al. and Amemiya et al. (1997) *Proceedings of the 1997 IS&T NIP13 International Conference on Digital Printing Technologies*, pp. 698-702.

The terms "acoustic coupling" and "acoustically coupled" used herein refer to a state wherein an object is placed in direct or indirect contact with another object so as to allow acoustic radiation to be transferred between the objects without substantial loss of acoustic energy. When two items are indirectly acoustically coupled, an "acoustic coupling medium" is needed to provide an intermediary through which acoustic radiation may be transmitted. Thus, an ejector may be acoustically coupled to a fluid in a reservoir, by, for example, interposing an acoustic coupling medium between the ejector and the fluid to transfer acoustic radiation generated by the ejector through the acoustic coupling medium and into the fluid.

An "acoustically activatable" moiety is a moiety that is caused to vibrate at an ultrasonic frequency when irradiated with acoustic energy of a particular wavelength.

The term "reservoir" as used herein refers to a receptacle or chamber for holding or containing a fluid. In its one of its simplest forms, a reservoir consists of a solid surface having sufficient wetting properties to hold a fluid merely due to contact between the fluid and the surface. A reservoir may also be a well within a well plate, a tube or other such container in a tube rack, and the like.

The term "array" as used herein refers to a two-dimensional arrangement of features, such as an arrangement of reservoirs, e.g., wells in a well plate. Arrays are generally comprised of features regularly ordered in, for example, a rectilinear grid, parallel stripes, spirals, and the like, but non-ordered arrays may be advantageously used as well. An array differs from a pattern in that patterns do not necessarily contain regular and ordered features. Arrays typically, but do not necessarily, comprise at least about 4 to about 10,000,000 features, generally in the range of about 4 to about 1,000,000 features.

The term "fluid" as used herein, as in a "fluid medium," refers to matter that is nonsolid and at least partially composed of a liquid. A fluid may contain a solid that is minimally, partially or fully solvated, dispersed or suspended. Examples of fluids include, without limitation, aqueous liquids (including water per se and salt water) and nonaqueous liquids such as organic solvents and the like. The fluid may also be a biological fluid containing cells, biomolecules, or the like.

The term "nucleic acid" refers to a nucleoside, nucleotide, or polynucleotide, including an oligonucleotide, whether generated in nature or synthesized in the laboratory, and as such encompasses non-natural constructs such as plasmids. The terms are used interchangeably herein unless specifically indicated otherwise or context dictates a different interpretation. Nucleic acids include those containing 2-deoxy-D-ribose as well as D-ribose, and thus encompass polydeoxyribonucleotides and polyribonucleotides, respectively, and may contain any of the conventional purine and pyrimidine bases, i.e., adenine (A), thymine (T), cytosine (C), guanine (G) and uracil (U), as well as protected forms thereof, e.g., wherein the base is protected with a protecting group such as acetyl, difluoroacetyl, trifluoroacetyl, isobutyryl or benzoyl, and purine and pyrimidine analogs, known to those skilled in the art and described in the pertinent texts and literature. Common analogs include, but are not limited to, 1-methyladenine, 2-methyladenine, $N^6$-methyladenine, $N^6$-isopentyl-adenine, 2-methylthio-$N^6$-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluoro-uracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl) uracil, 5-(methyl-aminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine. Nucleic acids herein may other types of modifications as well including, without limitation: modifications on the sugar moiety, e.g., wherein one or more of the hydroxyl groups are replaced with halogen atoms or aliphatic groups, or are functionalized as ethers, amines, or the like; nonnatural internucleotide linkages, such as methyl phosphonates, phosphotriesters, phosphoramidates, carbamates, phosphorothioates, phosphorodithioates, aminoalkyl phosphoramidates, and aminoalkyl phosphotriesters; functionalization with pendant moieties; incorporation of intercalators (e.g., acridine, psoralen, etc.); incorporation of chelators (e.g., metals, radioactive metals, boron, oxidative metals), and the like.

The term "polypeptide" is intended to include any structure comprised of two or more amino acids, and thus includes dipeptides, oligopeptides, and proteins, and these terms are used interchangeably herein unless the text or context indicates otherwise. The amino acids forming all or a part of a peptide may be any of the twenty conventional, naturally occurring amino acids, i.e., alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W), and tyrosine (Y), as well as non-conventional amino acids such as isomers and modifications of the conventional amino acids, e.g., D-amino acids, non-protein amino acids, post-translationally modified amino acids, enzymatically modified amino acids, β-amino acids, constructs or structures designed to mimic amino acids (e.g., α,α-disubstituted amino acids, N-alkyl amino acids, lactic acid, β-alanine, naphthylalanine, 3-pyridylalanine, 4-hydroxyproline, O-phosphoserine, N-acetylserine, N-formylmethionine, 3-methylhistidine, 5-hydroxylysine, and norleucine), and other non-conventional amino acids, as described, for example, in U.S. Pat. No. 5,679,782 to Rosenberg et al. Peptides may also contain nonpeptidic backbone linkages, wherein the naturally occurring amide —CONH— linkage is replaced at one or more sites within the peptide backbone with a non-conventional linkage such as N-substituted amide, ester, thioamide, retropeptide (—NHCO—), retrothioamide (—NHCS—), sulfonamido (—SO$_2$NH—), and/or peptoid (N-substituted glycine) linkages. Accordingly, peptides can include pseudopeptides and peptidomimetics. Peptides can be (a) naturally occurring, (b) produced by chemical synthesis, (c) produced by recombinant DNA technology, (d) produced by biochemical or enzymatic fragmentation of larger molecules, (e) produced by methods resulting from a combination of methods (a) through (d) listed above, or (f) produced by any other means for producing peptides.

The term "substantially" as in, for example, the phrase "substantially identical reservoirs" refers to reservoirs that do not materially deviate in acoustic properties. For example, acoustic attenuations of "substantially identical reservoirs" deviate by not more than 10%, preferably not more than 5%, more preferably not more than 1%, and most preferably at most 0.1% from each other. Other uses of the term "substantially" involve an analogous definition.

The invention provides a method for transfecting cells using acoustic radiation in a manner that enables transfection of a variety of cell types, including non-mammalian cells and mammalian cells, confluent cells and non-confluent cells. Using sonoporation as described herein, the method enables incorporation of exogenous material into host cells, including, without limitation, plasmids, ribonucleoproteins, and other species. As will be described in detail infra, the method lends itself to use in high-throughput transfection, in large part because the method can be carried out with large numbers of cell-containing reservoirs in succession.

In one embodiment, the method for transfecting cells comprises: (a) providing a system that includes (i) at least two reservoirs each containing host cells and exogenous material to be introduced into the host cells via sonoporation-induced transfection, and (ii) an acoustic radiation generator to generate and direct acoustic radiation; (b) acoustically coupling the acoustic radiation generator to a first of the reservoirs without simultaneously acoustically coupling the acoustic radiation generator to any other of the reservoirs; (c) activating the acoustic radiation generator to generate and direct acoustic radiation into the first reservoir in a manner that induces sonoporation of the host cells, thereby facilitating introduction of the exogenous material into the sonoporated host cells; (d) acoustically decoupling the acoustic radiation generator from the first reservoir; (e) acoustically coupling the acoustic radiation generator to a second of the reservoirs without simultaneously acoustically coupling the acoustic radiation generator to any other of the reservoirs; and (f) repeating step (c) with respect to the second reservoir.

Generally, although not necessarily, the first and second reservoirs are contained within a plurality of reservoirs, and the method is repeated with some or all of the reservoirs. When this is the case, the method includes an additional step following (f), namely, (g) acoustically decoupling the acoustic radiation generator from the second reservoir, and repeating steps (b) through (g) with respect to the other reservoirs. To provide modularity and interchangeability of components, it may sometimes be preferred for the device to be used in conjunction with a plurality of removable reservoirs, e.g., tubes in a tube rack or the like. The reservoirs are arranged in a pattern or an array, typically an array, to provide each reservoir with individual systematic addressability. While each of the reservoirs may be provided as a discrete or stand-alone container, in circumstances that require a large number of reservoirs, e.g., in a high-throughput transfection method, it is preferred that the reservoirs are contained within an integrated multiple reservoir unit. The multiple reservoir unit may be a well plate with the individual wells serving as reservoirs. Many well plates suitable for use with the device are commercially available and may contain, for example, 96, 384, 1536, or 3456 wells per well plate, and having a full skirt, half skirt, or no skirt. Well plates or microtiter plates have become commonly used laboratory items. The Society for Laboratory Automation and Screening (SLAS) has established and maintains standards for microtiter plates in conjunction with the American National Standards Institute, including the footprint and dimension standards ANSI/SLAS 1-2004. The wells of such well plates are generally in the form of rectilinear arrays.

The availability of such commercially available well plates does not preclude the manufacture and use of custom-made well plates in other geometrical configurations containing at least about 10,000 wells, or as many as 100,000 to 500,000 wells, or more. Furthermore, the material used in the construction of reservoirs must be acoustically compatible as well as compatible with the fluid samples contained therein. For water-based fluids, a number of materials are suitable for the construction of reservoirs and include, but are not limited to, ceramics such as silicon oxide and aluminum oxide, metals such as stainless steel and platinum, and polymers such as polyester, polypropylene, cyclic olefin copolymers (e.g., those available commercially as Zeonex® from Nippon Zeon and Topas® from Ticona), polystyrene, and polytetrafluoroethylene.

In addition, to reduce the amount of movement and time needed to transfect host cells in each of a plurality of reservoirs in rapid succession, it is preferred that the center of each reservoir be located not more than about 1 centimeter, e.g., not more than about 1.5 millimeters, not more than about 1 millimeter, and not more than about 0.5 millimeter from a neighboring reservoir center. These dimensions tend to limit the size of the reservoirs to a maximum volume. The reservoirs are constructed to contain typically no more than about 1 mL, preferably no more than about 500 μL, and more preferably no more than about 250 μL of fluid, and in some cases no more than 100 μL, 50 μL, 25 μL, 10 μL, 5 μL, 1 μL, or 0.5 μL of fluid. The volume of fluid medium in the reservoirs, during operation, is thus in the range of about 0.5 μL to about 500 μL. To facilitate consistency, it is also preferred that the reservoirs be substantially acoustically indistinguishable.

An acoustic radiation generator comprising an ultrasonic transducer is used to generate acoustic radiation and direct the acoustic radiation generated into the reservoir containing the host cells to be transfected. An ultrasonic transducer typically includes an actuator and a focusing element that concentrates acoustic energy produced by the actuator; examples of actuators include piezoelectric and magnetorestrictive elements, with piezoelectric transducers generally, although not necessarily, preferred herein. In operation, the actuator is driven by a signal at an ultrasonic driving frequency and produces ultrasonic vibrations in the active physical element. These vibrations are transmitted into and through an acoustic coupling medium and into the reservoir housing the fluid sample. A single transducer can be used, or in some cases, multiple element acoustic radiation generators comprising transducer assemblies may be used. For example, linear acoustic arrays, curvilinear acoustic arrays or phased acoustic arrays may be advantageously used to generate acoustic radiation that is transmitted simultaneous to a plurality of reservoirs. In a preferred embodiment, a single acoustic radiation generator is employed. Some examples of acoustic radiation generators that can be advantageously used herein are those incorporated into the Acoustic Droplet Ejection (ADE) systems available from Labcyte Inc. (San Jose, Calif.) and described, for instance, in U.S. Pat. No. 6,416,164 to Stearns et al.; U.S. Pat. No. 6,666,541 to Ellson et al.; U.S. Pat. No. 6,603,118 to Ellson et al.; U.S. Pat. No. 6,746,104 to Ellson et al.; U.S. Pat. No. 6,802,593 to Ellson et al.; U.S. Pat. No. 6,938,987 to Ellson et al.; U.S. Pat. No. 7,270,986 to Mutz et al.; U.S. Pat. No. 7,405,395 to Ellson et al.; and U.S. Pat. No. 7,439,048 to Mutz et al. Examples of commercially available ADE systems from Labcyte include the Echo® 500-series Liquid Handler systems, including the Echo® 525, the Echo® 550, and the Echo® 555 Liquid Handlers.

As explained above, the acoustic radiation generator herein preferably includes a focusing element. Any of a variety of focusing means that include curved surfaces or Fresnel lenses known in the art may be employed in conjunction with the present invention. Such focusing means are described in U.S. Pat. No. 4,308,547 to Lovelady et al. and U.S. Pat. No. 5,041,849 to Quate et al., as well as in U.S. Patent Application Publication No. 2002037579.

When transfecting host cells in each of a plurality of reservoirs, as in a well plate or other type of array, the method is carried out in conjunction with a means for positioning each of the reservoirs and an acoustic radiation generator in acoustic coupling relationship, such that after each sonoporation event, the acoustic radiation generator is aligned with the next reservoir to be irradiated. The positioning means may be incorporated into the transfection system in order to move a substrate containing the reservoirs (which may be positioned on a movable stage, for instance) relative to the acoustic ejector, or vice versa. Rapid and successive irradiation of reservoirs is thereby readily facilitated. Either type of positioning means, i.e., an ejector positioning means or a reservoir or reservoir substrate positioning means, can be constructed from, for example, motors, levers, pulleys, gears, a combination thereof, or other electromechanical or mechanical means. The reservoir-to-reservoir transition time is preferably at most about 0.5 seconds, preferably at most about 0.1 seconds, and optimally at most about 0.001 seconds.

It should be noted that the acoustic radiation generator must be in acoustic coupling relationship with respect to the reservoir to be irradiated and thus to the reservoir contents as well, and that, when successively irradiating multiple reservoirs, the acoustic radiation generator decouples from each irradiated reservoir after sonoporation, and is then acoustically coupled to the next reservoir for the next sonoporation event. The process thus involves acoustically coupling the acoustic radiation generator to a first reservoir to be irradiated, irradiating the first reservoir, then acoustically decoupling the acoustic radiation generator from the first reservoir, then acoustically coupling the acoustic radiation generator to the next reservoir, irradiating the next reservoir, etc., and continuing the process until the desired number of reservoirs has been irradiated. Although it is possible to achieve acoustic coupling through direct contact with the contents of the reservoirs, the preferred approach is to acoustically couple the acoustic radiation generator to a reservoir and thus to the contents thereof without allowing any portion of the acoustic radiation generator (e.g., the focusing means) to contact the contents of the reservoir.

The acoustic radiation generator may be in either direct contact or indirect contact with the external surface of each reservoir. With direct contact, in order to acoustically couple the acoustic radiation generator to a reservoir, it is preferred that the direct contact be wholly conformal to ensure efficient acoustic energy transfer. That is, the acoustic radiation generator and the reservoir should have corresponding surfaces adapted for mating contact. Thus, if acoustic coupling is achieved between the acoustic radiation generator and reservoir through the focusing means, it is desirable for the reservoir to have an outside surface that corresponds to the surface profile of the focusing means. Without conformal contact, efficiency and accuracy of acoustic energy transfer may be compromised. In addition, since many focusing means have a curved surface, the direct contact approach may necessitate the use of reservoirs that have a specially formed inverse surface.

Optimally, acoustic coupling is achieved between the acoustic radiation generator and each reservoir through indirect contact, as described in U.S. Pat. No. 6,416,164 to Stearns et al.; U.S. Pat. No. 6,666,541 to Ellson et al.; U.S. Pat. No. 6,603,118 to Ellson et al.; U.S. Pat. No. 6,746,104 to Ellson et al.; U.S. Pat. No. 6,802,593 to Ellson et al.; U.S. Pat. No. 6,938,987 to Ellson et al.; U.S. Pat. No. 7,270,986 to Mutz et al.; U.S. Pat. No. 7,405,395 to Ellson et al.; and 7,439,048 to Mutz et al., cited supra and incorporated by reference herein. Generally, an acoustic coupling medium is placed between the acoustic radiation generator and the base of the reservoir to be irradiated. The acoustic coupling medium may be an acoustic coupling fluid, preferably an acoustically homogeneous material in conformal contact with the uppermost surface of the acoustic radiation generator, e.g., with an acoustic focusing means located on the uppermost surface of the acoustic radiation generator, and the underside of the reservoir. In addition, it is important to ensure that the acoustic coupling fluid is substantially free of material having different acoustic properties than the fluid medium in the reservoir being irradiated. In use, a first reservoir is acoustically coupled to the acoustic radiation generator such that acoustic radiation generated by the acoustic radiation generator is directed, e.g., by the focusing means, into the acoustic coupling medium, which then transmits the acoustic radiation into the reservoir. The system may contain a single acoustic ejector, or, as noted previously, it may contain multiple ejectors. Single ejector designs are generally preferred over multiple ejector designs because accuracy of droplet placement and consistency in droplet size and velocity are more easily achieved with a single ejector. However, the invention is not limited to single ejector designs.

As explained earlier herein, a reservoir containing host cells to be transfected via sonoporation contains the host cells as well as the exogenous material to be introduced into the host cells. The host cells and the exogenous material are advantageously contained in a fluid medium, i.e., a host cell compatible fluid medium, such as a buffer, e.g., an isotonic buffer such as Dulbecco's phosphate buffered saline (DPBS). By a "compatible" fluid medium is meant one that the cells can survive in for at least five minutes.

Host cells and host cell types: Cells should be grown in appropriate medium with all necessary factors, and the medium must be free of contamination. Cell density in the fluid medium contained within a reservoir should be optimized, as too low a density can cause poor growth in the absence of cell-to-cell contact, and too high a density can result in contact inhibition, making cells resistant to uptake of nucleic acid or other macromolecules. Host cells are commonly derived from cells taken from a subject, such as a cell line. Many types of mammalian cells can be transfected using the method of the invention, including not only those mammalian cell lines that are commonly worked with but also, in some cases, cells that are extremely difficult to transfect by prior known methods. Commonly worked with mammalian cell lines include, for instance, the human cell lines HeLa, HepG2, HUVEC, MCF7, H1 human embryonic, GM12878, K562, and Jurkat E6.1; the mouse cell lines NIH-3T3 and MEFs (mouse embryonal fibroblasts); and other cell lines such as Chinese hamster ovary (CHO) cells and African green monkey kidney (COS-7) cells. Cells that are normally very difficult to transfect, but that may be efficiently transfected using the present method, include, by way of example: lymphocytes, including both B-cells and T-cells; primary cells of all origins; neurons; stem cells of all types; and oocytes. Specific cell lines within this latter group include the human lymphoblastoid lines GM12878 and Jurkat E6.1, and H1 human embryonic cells.

Specific examples of cell lines that can be transfected using the present method, include, without limitation, C8161, CCRF-CEM, MOLT, mIMCD-3, NHDF, HeLa-S3, Huh1, Huh4, Huh7, HUVEC, HASMC, HEKn, HEKa, MiaPaCell, Pancl, PC-3, TF1, CTLL-2, C1R, Rat6, CV1, RPTE, A10, T24, J82, A375, ARH-77, Calul, SW480, SW620, SKOV3, SK-UT, CaCo2, P388D1, SEM-K2, WEHI-231, HB56, TIB55, Jurkat, J45.01, LRMB, Bcl-1, BC-3, IC21, DLD2, Raw264.7, NRK, NRK-52E, MRCS, MEF, Hep G2, HeLa B, HeLa T4, COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts; 10.1 mouse fibroblasts, 293-T, 3T3, 721, 9L, A2780, A2780ADR, A2780cis, A 172, A20, A253, A431, A-549, ALC, B16, B35, BCP-1 cells, BEAS-2B, bEnd.3, BHK-21, BR 293. BxPC3. C3H-10T1/2, C6/36, Cal-27, CHO, CHO-7, CHO-IR, CHO-K1, CHO-K2, CHO-T, CHO Dhfr-/-, COR-L23, COR-L23/CPR, COR-L23/5010, COR-L23/R23, COS-7, COV-434, CML T1, CMT, CT26, D17, DH82, DU145, DuCaP, EL4, EM2, EM3, EMT6/AR1, EMT6/AR10.0, FM3, H1299, H69, HB54, HB55, HCA2, HEK-293, HeLa, Hepa1c1c7, HL-60, HMEC, HT-29, Jurkat, JY cells, K562 cells, Ku812, KCL22, KG1, KYO1, LNCap, Ma-Mel 1-48, MC-38, MCF-7, MCF-10A, MDA-MB-231, MDA-MB-468, MDA-MB-435, MDCK II, MDCK 11, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-1A/PNT 2, RenCa, RIN-5F, RMA/RMAS, Saos-2 cells, Sf-9, SkBr3, T2, T-47D, T84, THP1 cell line, U373, U87, U937, VCaP, Vero cells, WM39, WT-49, X63, YAC-1, YAR, and transgenic varieties thereof. Cell lines are available from a variety of sources known to those with skill in the art (see, e.g., the American Type Culture Collection (ATCC) (Manassas, Va.).

The exogenous material in the fluid medium containing the host cells, i.e., the exogenous material to be incorporated into the host cells via transfection, can be any material that can be introduced into a living cell to provide an intended function, result, or benefit. While transfection is generally defined as introducing molecules into a recipient cell so as to add to, alter, and/or regular the cell's DNA, that definition can be expanded in the present context insofar as the method of the invention facilitates the incorporation of a wide variety of molecular moieties into a host cell, including but not limited to molecular moieties that ultimately affect the structure and function of host cell DNA. "Exogenous material," as that term is used herein, then, includes, without limitation: nucleic acids such as DNA, RNA, mRNA, small interfering RNA (siRNA/RNAi), micro RNA (miRNA), DNA plasmids encoding genes that will express proteins in the host cell, DNA plasmids that serve other purposes like generating enhancers or RNA), small linear DNA encoding a moiety of interest such as a homologous recombination donor for CRISPR; proteins and polypeptides, including kinases, cytokines, chromatin remodeling enzymes, fluorescent proteins for visualization, and mutant versions of normal proteins; and small molecules, particularly low molecular weight (<about 900 daltons) organic compounds that are biologically useful (e.g., that may help regulate a biological process), such as inhibitors or activators of specific pathways (e.g., drug or toxin pathways), radioactively labeled nucleotides or amino acids, cholesterol, glucose and other sugars, and the like (see, e.g., the NCBI BioSystems Database entries under "Small Molecules"); lipidic and saccharidic materials such as lipids, lipoproteins, lipopolysaccharides, lipopolysaccharides, and polysaccharides; and ribonucleoproteins such as the Cas proteins and protein complexes used in CRISPR editing.

In a preferred embodiment, the exogenous material comprises a nucleic acid, such as a DNA plasmid, or a ribonucleoprotein, such as a Cas:guide RNA ribonucleoprotein.

Nucleic acids: Exogenous nucleic acids that can be introduced into the host cells may be in the form of genes, gene fragments, oligonucleotides and polynucleotides, or antisense oligonucleotides and polynucleotides, or may be any other type of nucleic acid having biological activity or other benefit. The nucleic acids introduced into host cells using the present method are generally, although not necessarily, in the form of constructs that include at least one structural gene under the transcriptional and translational control of a suitable regulatory region, e.g., a promoter sequence in a vector that may be a plasmid, in turn enabling expression of the peptide or protein encoded by the aforementioned structural gene. Such constructs usually contain one or more regulatory elements other than promoters, as is known in the art. Most commonly, an exogenous nucleic acid is introduced into a host cell using the present method by means of a DNA plasmid. Other suitable vectors are known and described in the pertinent texts and literature. Transfection of host cells with a nucleic acid may in some cases require a transfection facilitator such as a cationic lipid formulation, a cationic polymer (e.g., DEAE-dextran or polyethylenimine), a dendrimer, or the like. The method of the invention, as alluded to above, works in combination with CRISPR (clustered regularly interspaced short palindromic repeats) plasmids, as established in Example 5. When transfecting host cells with CRISPR plasmids, some minor modifications may be necessary or desirable; for instance, a CRISPR plasmid, because it is relatively large, may be subjected to an upstream treatment to reduce its overall size. In the alternative, or in addition, a transfection helper reagent such as JetPEI® (Polyplus Transfection) may be used.

CRISPR and RNPs: It should be emphasized that the present methods are useful in conjunction with a wide variety of proteins, including ribonucleoproteins (RNPs). An RNP is a protein bound to RNA, i.e., it is a complex of a ribonucleic acid and an RNA-binding protein. Such complexes are important in a number of biological functions, including DNA replication and regulation of gene expression. Of particular significance in the present context are engineered RNPs that leverage the CRISPR-Cas mechanism, which has recently taken on enormous significance in the field of genome editing; see, e.g., Donohoue et al., *Trends Biotechnol*. (Aug. 1, 2017). As is known in the art, CRISPR-based transfection involves the use of RNPs composed of a CRISPR-associated protein, or "Cas" protein, and RNA, i.e., a "guide RNA" (gRNA), which may either a combination of crRNA (which locates the target sequence of host DNA) and tracrRNA (which base pairs with the crRNA to form an RNA duplex), or a single guide RNA (sgRNA), which incorporates both crRNA and tracrRNA.

The Cas protein, usually Cas9 or a homolog thereof, and a guide RNA, either "single guide" RNA (sgRNA) or a combination of crRNA and tracrRNA, are the primary components of a CRISPR transfection system. Variations of the CRISPR components are possible and described, for example, in U.S. Pat. No. 8,771,945 to Zhang et al., incorporated by reference in its entirety. While Cas9, such as Cas9 from *S. pyogenes* or *S. pneumoniae*, is the CRISPR nuclease most commonly used, it will be appreciated that other Cas proteins can be used in place of Cas9, particularly Cfp1, with other Cas proteins including, without limitation, Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. A Cas protein used herein in conjunction with CRISPR transfection may be altered or modified in one of various ways, e.g., a mutated Cas nuclease that lacks the ability to cleave one or both strands of a target polynucleotide can be useful in many contexts. For instance, CRISPR-Cas9 D10A nickase, containing an aspartate-to-alanine substitution (D10A) in the RuvC I catalytic domain of Cas9 from *S. pyogenes*, cleaves a single strand of a polynucleotide duplex instead of a double strand. As another example, "dCas9," which contains the aforementioned mutation as well as an H840A mutation in the HNH domain, completely lacks the ability to cleave a polynucleotide. See, e.g., Qi et al. (2013) *Cell* 152: 1173-1183. As a further example, the Cas nuclease is part of a fusion protein, in which the fused protein domain is selected to provide an added function, e.g., transcription activation or repression activity, nucleic acid binding activity, or the like.

In general, a guide sequence is any polynucleotide sequence having sufficient complementarity with a target polynucleotide sequence to hybridize with the target sequence and direct sequence-specific binding of a CRISPR complex to the target sequence. A guide sequence may be selected to target any target sequence. In some embodiments, the target sequence is a sequence within a genome of a cell, particularly a sequence that is unique in the target genome. The guide sequence may be selected to enable the targeting of a polynucleotide in a host cell for any number of purposes, modifying the target polynucleotide by deleting, inserting, translocating, inactivating, or activating targeted regions. The CRISPR complex therefore has a broad spectrum of applications in many fields, including gene therapy, drug screening, disease diagnosis, and prognosis. Accordingly, the target polynucleotide of a CRISPR complex may include a number of disease-associated genes and polynucleotides as well as signaling biochemical pathway-associated genes and polynucleotides. Many disease-associated genes and polynucleotides are known in the art, as are signaling biochemical pathway-associated genes and polynucleotides; see, e.g., U.S. Pat. No. 8,771,945 to Zhang et al., supra.

The present method for sonoporating host cells includes a means for imparting the acoustic radiation generated by the acoustic radiation generator to the host cells. Generally, although not necessarily, the means for imparting acoustic radiation to the host cells comprises a transfection excitation material, i.e., a material that is caused to vibrate ultrasonically upon irradiation with the acoustic radiation generator, and that transfers the ultrasonic vibrations to neighboring host cells. The transfection excitation material may comprise a plurality of acoustically activatable moieties in the form of particles, beads, or localized fluid volumes, where a "localized fluid volume" refers to a spatially localized volume of fluid, which may or may not be circumscribed by a delineating feature, and wherein the localized fluid volume will usually have different physical properties than the surrounding fluid, although this is not required. Uncircumscribed localized fluid volumes include fluidic compositions wherein localized lipidic, or hydrophobic, regions are contained within a hydrophilic (e.g., aqueous) fluid, or wherein localized hydrophilic (e.g., aqueous) regions are contained within a lipidic, or hydrophobic fluid. Circumscribed localized fluid volumes include fluid-containing microcapsules, e.g., liquid-containing and gel-containing microcapsules, wherein the capsule wall may or may not allow for some exchange of material between the capsule interior and the external fluid, and wherein the fluid may or may not contain suspended particles. Still other types of circumscribed volumes are comprised of a first fluid that may or may not be immiscible with the fluid in which it is contained, wherein a molecular layer of an immiscible material circumscribes the first fluid so as to provide a barrier between the fluidic interior and the fluidic exterior. See, e.g., U.S. Pat. No. 7,270,986 to Mutz et al.

In one embodiment of the invention, the transfection excitation material comprises gas-filled microbubbles that are incorporated into the fluid medium along with the host cells and the exogenous material.

The microbubbles used in a preferred embodiment herein are small spheres encapsulating a gas core within a shell having an outer surface that can be functionalized, e.g., by attachment of a targeting ligand. The targeting ligand will sometimes be hereinafter referred to as a "first binding moiety," insofar as the targeting ligand can associate with a second binding moiety present on an antibody specific for the host cell, such that association of the first and second binding moieties results in a microbubble-host cell complex. Formation of the microbubble-host cell complex is one technique for ensuring that the acoustic radiation received by the microbubbles and causing them to vibrate is transmitted to the host cells, facilitating sonoporation. Without wishing to be bound by theory, transmitting acoustic radiation to the host cells is believed to facilitate sonoporation by physically disrupting the cell membrane or cell wall, creating transient pores that allow cellular uptake of large molecules such as DNA or an RNP.

Examples of typical microbubble materials, i.e., typical shell materials, include, without limitation, lipids, polymers, albumin, and galactose, although lipidic materials are most commonly used. Other types of shell materials that are longer lasting, i.e., resistant to degradation (via biodegradation or other processes), can also be used, e.g., coated glass beads or cross-linked polymers (see U.S. Pat. No. 5,487,390 to Cohen et al., incorporated by reference herein). Suitable microbubbles include microsphere-type products used in medical contrast imaging (i.e., in contrast-enhanced ultrasound), cell isolation, and cell separation. Accordingly, shell materials described in U.S. Patent Application Publication No. 2015/0219636 A1 to Rychak et al. (applicant Targeson, Inc., San Diego, Calif.), which pertains to use of microbubble contrast agents in various contexts, can also be used in conjunction with the present method. The disclosure of the aforementioned patent application is incorporated by reference herein with respect to its disclosure of suitable microbubble shell materials and surface functionalization techniques. Preferred microbubble shell materials for use in conjunction with the invention are relatively elastic in order to minimize the likelihood of cavitation during sonoporation. The gas core of the microbubble can be a perfluorocarbon, air, or nitrogen, although perfluorocarbons are most common. It is the gas core of the microbubble that oscillates in an ultrasonic frequency field, which in turn causes the microbubbles to resonate during the present transfection method. Although the underlying mechanism has not been identified with clarity, it should be emphasized that acoustically induced resonance of microbubbles tethered to host cells as described herein is responsible for successful transfection.

Commercially available ultrasound contrast agents that can be advantageously used with the present invention include, by way of example: Targesphere® and Targesphere® SA (available from Targeson, San Diego, Calif.; see Tlaxa et al. (2010) *Ultrasound Med. Biol.* 36(11):1907-18); Optison® (GE Healthcare), albumin microbubbles with an octafluoropropane gas core; Levovist® (Schering), having a lipid/galactose shell and a core of air; Imagent® lipid microspheres with a perflexane core; Definity® lipid microspheres with an octafluoropropane gas core; and Lumason® sulfur hexafluoride lipid microbubbles (previously Sonovue®) and MicroMarker microbubbles (Bracco Imaging S.p.A./Fujifilm Visualsonics). Microbubbles intended for other purposes can also be used, such as the streptavidin-coated glass microbubbles available from Akadeum Life Sciences (Ann Arbor, Mich.).

In one embodiment of the invention, the microbubbles are conjugated to the host cells to facilitate transfer of acoustic energy from the irradiated microbubbles to the cells, thereby allowing transfection of exogenous material into the cells through the excited cell membrane or cell wall. Preparation of microbubble-antibody conjugates typically involves functionalization of the microbubbles with a first binding moiety, followed by combining the functionalized microbubbles with antibodies specific for the host cell type, where the antibodies are functionalized with a second binding moiety that links to the first binding moiety present on the microbubbles. Mixing is carried out in a host cell compatible fluid medium. In preparing the microbubble-antibody conjugates, the mass/volume ratio is typically in the range of about 0.5 µg to 5 µg antibody to $2 \times 10^7$ microbubbles, more typically in the range of about 0.5 µg to 3 µg antibody to $2 \times 10^7$ microbubbles, and most usually in the range of about 0.5 µg to 1.5 µg antibody to $2 \times 10^7$ microbubbles.

Attachment between the first binding moiety and the second binding moiety, i.e., the "binding pair" forming the linkage that results in the microbubble-cell complex, may be covalent or noncovalent, although binding is typically noncovalent. Examples of covalent attachment include an amide linkage formed between a free amino group that serves as one of the first and second binding moieties and a carboxyl group that serves as the other of the first and second binding moieties. Noncovalent modes of attachment include, for instance, ionic bonding, hydrogen bonding, adsorption or physical immobilization. Exemplary binding pairs include any haptenic or antigenic compound in combination with a corresponding antibody or binding portion or fragment thereof (e.g., digoxigenin and anti-digoxigenin; mouse immunoglobulin and goat anti-mouse immunoglobulin) and nonimmunological binding pairs (e.g., biotin-avidin, biotin-streptavidin, hormone [e.g., thyroxine and cortisol]-hormone binding protein, receptor-receptor agonist or antagonist (e.g., acetylcholine receptor-acetylcholine or an analog thereof), IgG-protein A, lectin-carbohydrate, enzyme-enzyme cofactor, enzyme-enzyme inhibitor, and complementary polynucleotide pairs capable of forming nucleic acid duplexes), and the like. Biotin-streptavidin attachments are most commonly used, typically using commercially available biotinylated antibodies, and microbubbles surface-functionalized with streptavidin.

"Loaded" microbubble-antibody conjugates can then prepared by mixing the microbubble-antibody conjugates with the exogenous material, where the exogenous material is as described earlier herein, e.g., a DNA plasmid or a CRISPR RNP. A preferred concentration/count ratio for loading the microbubble-antibody conjugates is in the range of about 1-10 µM RNP to $1.25 \times 10^7$ conjugates ($5 \times 10^8$ per mL), optimally in the range of about 3-6 µM RNP to $1.25 \times 10^7$ conjugates. These are representative ranges only, and are not intended to be limiting, insofar as suitable concentration/count ratios for any exogenous material can be determined empirically. At this point, the concentration of loaded microbubble-antibody conjugates in the fluid medium can be adjusted, e.g., by dilution with a host cell-compatible fluid, where the fluid may or may not be the same as the fluid medium used in step (a). The extent of dilution is optimized to provide an environment conducive to cell health and thus better transfection efficiency as well. Optimization of the extent of dilution is described in the Examples. It should be noted that, in general, a suspension that is too dilute will not provide a sufficient degree of transfection, while a suspension that is too concentrated will similarly provide an insufficient degree of transfection, although for different reasons; in the latter case, the acoustic energy may not reach many of the host cells, as they will essentially be shielded from the toneburst by the microbubble-antibody conjugates.

Sonoporation: The loaded microbubble-antibody conjugates are then irradiated by activating the acoustic radiation generator to generate and direct acoustic radiation into a reservoir containing the loaded conjugates in a fluid medium as described previously, using sonoporation parameters selected to bring about transfection. Suitable sonoporation parameters can be selected empirically, by correlating observed transfection efficiency with respect to one or more sonoporation parameters, such as acoustic intensity, transducer output frequency, and toneburst profile (e.g., toneburst width). For instance, as explained earlier, the acoustic pressure used in irradiating a reservoir containing host cells, microbubbles, and the selected exogenous material, should be sufficient to induce resonance of the microbubbles but, in a preferred embodiment, not be so high as to cause microbubble cavitation in the fluid region in the vicinity of the acoustic focal spot, which is usually located on the inner surface of the reservoir bottom. Typical acoustic pressures at the focal spot are in the range of about 1 MPa to about 2 MPa. Optimal sonoporation parameters may be determined by those of ordinary skill in the art using routine experimentation, and will generally vary with cell type. Generally, however, sonoporation is conducted by irradiating the reservoir with short bursts of a cyclic acoustic toneburst each on the order of tens of milliseconds or less and occurring at about 10 to about 25 times per second for about 15-40 seconds, e.g., irradiating at less than 1 ms duration 10 times per second (10 Hz) for about 30 seconds. By way of illustration, Example 6 describes sonoporation with using the aforementioned protocol, irradiating with 300 cyclic acoustic tonebursts at a burst repetition rate of 10 Hz (corresponding to a sonoporation time period of about 30 seconds, as indicated above), with each toneburst consisting of 8 cycles of output. In Example 6, the toneburst duration was approximately 3.5 µs (8 cycles divided by a nominal output frequency of 2.25 MHz). Irradiation can be repeated within any one reservoir, changing the location of the focal point or the width of the beam, if desired, to maximize the number and area of microbubbles that are sonoporated, in turn maximizing transfection efficiency.

Usually, it is preferred that the acoustic radiation generated be of a frequency and intensity selected to ensure that irradiated microbubbles receive excitation radiation having a wavelength within about 15% of the average resonance frequency of the microbubbles in the reservoir, preferably within about 5% of the average resonance frequency of the microbubbles in the reservoir, or within about 15% of a harmonic of the average frequency of the microbubbles in the reservoir, preferably within about 5% of a harmonic of the average frequency of the microbubbles in the reservoir. In a related embodiment, the acoustic radiation generated may be of a frequency and intensity selected to ensure that irradiated microbubbles of a particular size or within a particular size range receive excitation radiation having a wavelength within about 15% of the average resonance frequency of the microbubbles in the reservoir, preferably within about 5% of the average resonance frequency of the microbubbles in the reservoir, or within about 15% of a harmonic of the average frequency of the microbubbles in the reservoir, preferably within about 5% of a harmonic of the average frequency of the microbubbles in the reservoir. If the microbubbles are in a composition with a multimodal size distribution, they can be irradiated more than once with each irradiation event targeting microbubbles having or near each modal peak.

In addition, while some microbubbles may undergo cavitation as a result of irradiation, it is generally preferred that cavitation be avoided. As such, sonoporation is usually conducted by adjusting the acoustic radiation generator to irradiate the microbubbles using an acoustic sonoporation pressure in the range of about 50% to 90% of the minimum acoustic pressure that would result in microbubble cavitation. The acoustic sonoporation pressure may be, for example, in the range of about 0.2 MPa to about 2 MPa, typically less than about 1.5 MPa. While for many cell lines acoustic power levels below the cavitation limit will provide good transfection results via sonoporation, an additional benefit of operating below the cavitation limit is that re-use of the microbubbles is then possible. That is, when irradiating with subcavitation acoustic energy, the number of intact microbubbles remaining after irradiation is generally within about 50%, 80%, 90%, or 99% of the original number of microbubbles prior to sonoporation. Post-sonoporation intact microbubbles can be re-used with the same host cells, which may or may not be in the same reservoir as the initially sonoporated host cells. Alternatively, if post-sonoporation intact microbubbles are separated from the conjugating antibody, either naturally or as a result of treatment, they can be re-used with a different host cell type. Operating at subcavitation acoustic levels also allows for repetition of irradiation in the same reservoir, wherein, for instance, after an initial sonoporation event, an acoustic beam generated by the acoustic radiation generator is used to bring intact, already irradiated microbubbles into contact with host cells in a different spatial location within the reservoir.

In other embodiments of the invention, as will be explained infra, sonoporation of does not require repetition of acoustic coupling and decoupling steps. The above description regarding host cells, exogenous material, fluid medium, transfection excitation material, and other elements and aspects of the transfection methodology is otherwise applicable to the following embodiments:

In an additional embodiment of the invention, then, an acoustic method is provided for transfecting cells by: acoustically coupling an acoustic radiation generator to a reservoir that contains host cells, exogenous material to be transfected into the host cells, and a fluid medium; and activating the acoustic radiation generator to generate acoustic radiation and direct the acoustic radiation into the reservoir in a manner that induces sonoporation of the host cells without resulting in a temperature increase in the fluid medium of greater than about 10° C. For instance, the method can induce sonoporation without resulting in a temperature increase of greater than about 5° C., 2° C., or 1° C. In a related embodiment, sonoporation takes place without raising the temperature of the fluid medium to greater than about 40° C. It is preferred that the acoustic radiation generated is directed into the reservoir using a focusing means, such that sonoporation is carried out using focused acoustic radiation. It is also preferred that the fluid medium contain a transfection excitation material as explained earlier herein.

In another embodiment, an acoustic method is provided for transfecting cells by acoustically coupling an acoustic radiation generator to a selected reservoir contained within an integral multiple reservoir unit comprising at least 1536 reservoirs, the selected reservoir containing host cells, exogenous material to be transfected into the host cells, and a fluid medium; and activating the acoustic radiation generator to generate acoustic radiation and direct the acoustic radiation into the reservoir in a manner that induces sonoporation of the host cells, thereby facilitating incorporation of the exogenous material into the sonoporated host cells. The integral multiple reservoir unit may, accordingly, be a microwell plate with 1536 wells, or with 3456 wells, or the like. As in the preceding embodiment, it is preferred that the acoustic radiation generated is directed into the reservoir using a focusing means and that the fluid medium contain a transfection excitation material.

In another embodiment, an acoustic method is provided for transfecting cells by acoustically coupling an acoustic radiation generator to a reservoir that contains host cells, exogenous material to be transfected into the host cells, a fluid medium, and a transfection excitation material comprised of a plurality of acoustically activatable localized fluid volumes; and activating the acoustic radiation generator to generate acoustic radiation and direct the acoustic radiation into the reservoir in a manner that acoustically activates the localized fluid volumes so that they vibrate at a frequency that is within about 15% of the average resonance frequency of the localized fluid volumes or within about 15% of a harmonic of the average resonance frequency of the localized fluid volumes, thereby facilitating incorporation of the exogenous material into host cells in the proximity of the acoustically activated localized fluid volumes. For instance, the localized fluid volumes may be acoustically activated so that they vibrate at a frequency that is within about 5% of the average resonance frequency of the localized fluid volumes or within about 5% of a harmonic of the average resonance frequency of the localized fluid volumes. Again, in a preferred embodiment, the acoustic radiation directed into the reservoir is focused acoustic radiation.

In another embodiment, an acoustic method for transfecting cells is provided that comprises: acoustically coupling an acoustic radiation generator to a reservoir that contains host cells, exogenous material to be transfected into the host cells, a fluid medium, and a transfection excitation material comprised of a plurality of acoustically activatable localized fluid volumes having a size distribution; and activating the acoustic radiation generator to generate acoustic radiation and direct the acoustic radiation into the reservoir in a manner that acoustically activates the localized fluid volumes having a size within about 15% of a selected size, thereby facilitating incorporation of the exogenous material into host cells in the proximity of the acoustically activated localized fluid volumes.

In a related embodiment, an acoustic method for transfecting cells is provided that comprises: (a) acoustically coupling an acoustic radiation generator to a reservoir that contains host cells, exogenous material to be transfected into the host cells, a fluid medium, and a transfection excitation material comprised of a plurality of acoustically activatable localized fluid volumes having a multimodal size distribution; (b) activating the acoustic radiation generator to generate acoustic radiation and direct the acoustic radiation into the reservoir in a manner that acoustically activates localized fluid volumes having a size that is within about 15% of a first modal peak, whereby the acoustically activated localized fluid volumes transfer acoustic energy to nearby host cells; (c) repeating step (b) to acoustically activate localized fluid volumes having a size that is within about 15% of a second modal peak; and (d) optionally repeating step (b) to acoustically activate localized fluid volumes having a size that is within about 15% of one or more additional modal peaks.

In an additional embodiment, an acoustic method is provided for transfecting cells, the method comprising: acoustically coupling an acoustic radiation generator to a reservoir containing host cells, exogenous material to be transfected into the host cells, a fluid medium, and a transfection excitation material comprised of a plurality of acoustically activatable localized fluid volumes having a size distribution; and activating the acoustic radiation generator to generate acoustic radiation having a selected frequency content and direct the acoustic radiation generated into the reservoir in a manner that induces sonoporation of the host cells, wherein the frequency content of the acoustic radiation generated is selected to correlate with the size distribution of the acoustically activatable localized fluid volumes. By "correlate with" is meant that individual frequencies within the acoustic radiation are tuned to target and acoustically activate individual sizes and size ranges within the localized volume distribution.

In a related embodiment, an acoustic method for transfecting cells is provided by acoustically coupling an acoustic radiation generator to a reservoir containing host cells, exogenous material to be transfected into the host cells, a fluid medium, and a transfection excitation material comprised of a plurality of acoustically activatable localized fluid volumes having a spatial distribution within the reservoir; and activating the acoustic radiation generator to generate acoustic radiation having a selected frequency content and direct the acoustic radiation generated into the reservoir in a manner that induces sonoporation of the host cells, thereby facilitating incorporation of the exogenous material into the sonoporated host cells, wherein the frequency content of the acoustic radiation generated is selected to correlate with the spatial distribution of the acoustically activatable localized fluid volumes. In this case, "correlate with" indicates that individual frequencies within the acoustic radiation are tuned to target and acoustically activate localized volumes at different locations within the reservoir.

In another embodiment, sonoporation is conducted using two transducers operating in concert (preferably but not necessarily simultaneously) but at different frequencies, wherein one of the transducers is an annular transducer is operably mounted around and enclosing a standard transducer. In this embodiment, the annular transducer and the standard transducer will generally operate at different frequencies. For instance, when the sonoporated cells are to be acoustically ejected from the fluid medium, the annular transducer may operate at a frequency selected to bring about sonoporation, while the standard transducer can be operated at a frequency effective to result in acoustic ejection of sonoporated cells, e.g., into a reservoir, onto a substrate, or for transport to an analytical instrument for analysis. In such a case, the annular transducer may operate at a frequency in the range of about 1 MHz to about 2.5 MHz, and the standard transducer may operate at a frequency in the range of about 6 MHz to about 20 MHz, preferably in the range of about 9 MHz to about 14 MHz, and optimally about 11.5 MHz.

In one aspect of this embodiment, one of the two transducers primarily functions to supply the acoustic energy for sonoporation and the other transducer delivers acoustic energy to change the relative position of the microbubbles with respect to the host cells when microbubble-cell conjugation is not used. Ideally, when the microbubbles and the host cells are positioned in proximity of each other, it should be in a region of acoustic intensity effective to cause sonoporation.

In an additional embodiment, sonoporation involves irradiation with multiple acoustic tonebursts in succession, each having a different acoustic frequency effective to sonoporate differently sized microbubbles. The acoustic frequency of each of the multiple acoustic tonebursts is typically in the range of about 1.5 MHz to about 5.0 MHz, more usually in the range of about 2.0 MHz to about 2.5 MHz. A narrow distribution of microbubble sizes typically requires a smaller range of acoustic frequencies to achieve the same level of excitation as a broad distribution of microbubble sizes, where acoustic frequency would need to be varied to achieve the same effect. Optimally, the acoustic frequency content is adjusted in response to the distribution of resonance frequencies for the microbubbles to improve the uniformity of sonoporation and at the minimal amount of total delivered acoustic energy. The multiple acoustic tonebursts are commonly 5-cycle to 10-cycle tonebursts, and may be the same or different.

In a further embodiment, an acoustic method for transfecting cells is provided that comprises: acoustically coupling an acoustic radiation generator to a selected reservoir containing host cells, exogenous material to be transfected into the host cells, a fluid medium, and a transfection excitation material comprising a plurality of acoustically activatable localized fluid volumes; and activating the acoustic radiation generator to generate acoustic radiation and direct the acoustic radiation into the reservoir in a manner that acoustically activates the localized fluid volumes, thereby facilitating incorporation of the exogenous material into host cells in the proximity of the acoustically activated localized fluid volumes, wherein the acoustic radiation generated is at an acoustic sonoporation pressure selected to ensure that at least 50% of the localized fluid volumes remain intact after irradiation. In one aspect of this embodiment, the acoustic sonoporation is in the range of about 50% to about 90% of the minimum acoustic pressure that would result in cavitation of the localized fluid volumes.

The present disclosure is also intended to encompass various ways of optimizing the acoustic transfection process. For example, as described in U.S. Pat. No. 6,932,097 to Ellson et al., U.S. Pat. No. 6,938,995 to Ellson et al., U.S. Pat. No. 7,354,141 to Ellson et al., U.S. Pat. No. 7,899,645 to Qureshi et al., U.S. Pat. No. 7,900,505 to Ellson et al., U.S. Pat. No. 8,107,319 to Stearns et al., U.S. Pat. No. 8,453,507 to Ellson et al., and U.S. Pat. No. 8,503,266 to Stearns et al., an acoustic radiation generator as described herein can be utilized for characterization of a fluid in a reservoir, to measure the height of the fluid meniscus as well as other properties, such as fluid volume, viscosity, density, surface tension, composition, acoustic impedance, acoustic attenuation, speed of sound in the fluid, etc., any or all of which can then be used to determine optimum sonoporation parameters, including acoustic power, acoustic frequency, toneburst duration, and/or the F-number of the focusing lens. As another example, U.S. Pat. Nos. 7,717,544 and 8,770,691 to Stearns et al. describe a method for optimizing the amplitude of acoustic radiation used for acoustic droplet ejection or other acoustic processes, by analyzing the waveforms of acoustic radiation reflected from surfaces within the reservoir. In addition, U.S. Pat. No. 7,481,511 to Mutz et al. and U.S. Pat. No. 7,784,331 to Ellson et al. provide methods for controlling acoustic process parameters to account for variations in reservoir properties.

It is to be understood that while the invention has been described in conjunction with a number of specific embodiments, the foregoing description as well as the examples that follow are intended to illustrate and not limit the scope of the invention. Other aspects, advantages and modifications will be apparent to those skilled in the art. All patents, patent applications, and publications mentioned here are hereby incorporated by reference in their entireties.

EXPERIMENTAL

Materials:
The following list indicates the materials used in these examples, along with the material sources:
Targesphere® SA: Cationic dispersion of streptavidin-functionalized microbubbles (Targeson)
Anti-CD51: Biotinylated anti-human CD51 antibody, 0.5 µg/µL in DPBS containing 0.09% sodium azide (Biolegend #327906)
HEK-293 cells: Human embryonic kidney cells, cell line 293, in a standard cell culture buffer, DMEM with high glucose media, supplemented with 4 mM L-Glutamine, 10% fetal bovine serum (FBS), and 100 U/µL penicillin-streptomycin (ATCC #CRL-1773)
DPBS: Dulbecco's phosphate-buffered saline, with calcium and magnesium (ThermoFisher Scientific #14040182)
GFP: green fluorescent protein (eGFP, or enhanced GFP, was used throughout)
gWiz-GFP: eGFP-coded plasmid (Aldevron)
CRISPR plasmid: pCas-Guide-EF1a-eGFP (Origene #GE100018)
Lipofectamine® 3000 (ThermoFisher Scientific)
General Protocol for Examples 1-5:
(1) Preparation of microbubble/DPBS dispersion: A vial containing the Targesphere SA microbubble dispersion was gently shaken and inverted end-to-end for 10 seconds, until the mixture appeared uniformly opaque. 100 µL of the Targesphere SA dispersion was extracted and introduced into a new 1.5 mL tube. 900 µL DPBS was added, and the dispersion gently mixed. The mixture was then incubated upright at room temperature for 2 minutes, followed by spinning in a Minifuge® for 2 minutes to separate the microbubbles from the suspension liquid. Using a syringe needle, the infranatant below the white cake of microbubbles was slowly removed, and the microbubbles were then resuspended in 100 µL of DPBS. (The original medium was removed from the Targesphere SA microbubble dispersion and replaced with DPBS, in order to reduce surface tension problems and adherence of the bubbles to well surfaces seen with the original microbubble medium.) A modified version of this protocol was used in Example 6, as explained in that example.

(2) Conjugation of microbubbles to biotinylated antibody: 10 µg anti-CD51 biotinylated antibody (i.e., 20 µL of the 0.5 µg/µL solution) were added to 100 µL of the microbubble dispersion, such that the mass/vol ratio of anti-CD51 antibody to the Targesphere SA dispersion was 1:10. The vial was incubated at room temperature with gentle agitation for about 20 minutes. A modified version of this protocol was used in Example 6, as explained therein.

(3) Preparation of plasmid-loaded microbubbles (Examples 1-5): The vial containing the biotinylated antibody/Targesphere composition was inverted several times to uniformly mix, and 24 µL of gWiz-GFP plasmid at 5 µg/µL (corresponding to 120 µg gWiz-GFP) was added to the 120 µL of microbubble-biotinylated antibody conjugates prepared in (2), such that the mass/vol ratio of plasmid to the Targesphere SA dispersion was 1:1. The vial was again incubated at room temperature with gentle agitation for about 25 minutes.

(4) Incubation with cells: The following plasmid-loaded microbubble dilutions were prepared:

1:4 vol/vol, 100 µL microbubble dispersion with 300 µL DPBS;

1:20 vol/vol, 20 µL microbubble dispersion with 380 µL DPBS;

1:40 vol/vol, 10 µL microbubble dispersion with 390 µL DPBS; and

1:200 vol/vol, 2 µL microbubble dispersion with 398 µL DPBS.

400 µL DPBS, without microbubbles, was used as a control.

20 µL of the plasmid-loaded microbubbles (or control) were pipetted onto the plated HEK-293 cells, which had been cultured to 80% confluence in a 384-well plate (giving approximately 25,000 cells per well, with a maximum volume of approximately 115 µL/well), media having been removed from the cells via pipetting first. In the following table, treatment concentration is correlated with microbubble dilution, loading volume per well, and microbubble-to-cell incubation ratio:

TABLE 1

| Treatment Conc. (plasmid-loaded microbubble/mL) | Microbubble Dilution | Loading Vol. per Well (µL) | Microbubble:Cell Incubation Ratio |
|---|---|---|---|
| $1 \times 10^7$ | 1:200 | 20 | 10 |
| $5 \times 10^7$ | 1:40 | 20 | 50 |
| $1 \times 10^8$ | 1:20 | 20 | 100 |
| $5 \times 10^8$ | 1:4 | 20 | 500 |

The well plate was flipped upside down to facilitate binding, and was placed in a 37° C. incubator for 5 minutes. Originally, the plate was then washed with 50 µL DPBS to remove unbound microbubbles; having found that the washing step also removed cells, however, the washing step was discontinued (note: this may or may not be true for different cell types).

(5) Sonoporation: The wells were refilled with 80 µL pre-warmed DPBS for a total of 100 µL, and spun at 125 RCF for 5 minutes to remove large bubbles (higher spin speeds would likely have killed many if not most of the cells). The cells were then pulsed with ultrasound using an acoustic radiation generator in a modified version of an acoustic liquid handler (Echo® 500 series liquid handler, Labcyte Inc., San Jose Calif.), and the well plates returned to the incubator overnight. After 1-2 days, cells were examined for GFP fluorescence, indicative of DNA uptake, and survival.

Example 1

Using the above protocol, four plates of HEK-293 cells were tested. All four plates were set up identically, including DPBS-only control wells. The control plate was not sonicated. 384-well plates were used, with 25,000 HEK-293 cells per well. Each plate was pulsed with a single voltage, either 0 V (control plate), 0.5 V (low power), 1.0 V (medium power), or 1.5 V (high power), where 1.0 V resulted in an acoustic pressure at the focal spot of about 1.5 MPa. 24 hours post-sonoporation, the cells were examined for GFP fluorescence. It was found that sonoporation was successful in enabling the HEK-293 cells to take up and express the GFP plasmid, and that the percent uptake increased with voltage and the concentration of plasmid-loaded microbubbles. The highest degree of fluorescence was found with the highest concentration of plasmid-loaded microbubbles and at the highest voltage. Green (fluorescent) cells were concentrated around the perimeter of the wells due to the distribution of the microbubbles following inversion of the well plate. Some cells in the control plate turned green, but very few; this was due to a small percentage of cells taking up plasmid in the media.

Example 2

The procedures of the General Protocol and Example 1 were follows, except that a "plasmid only" control was substituted for the 1:200 dilution, i.e., plasmid was added at the same concentration found in the 1:4 wells. The results obtained confirmed that high media concentrations of plasmid alone were not sufficient to transform cells.

Example 3

The procedures of the General Protocol Example 1 were repeated, but rather than single pulses applied to the center of each well, each well was pulsed several times at different locations. This was found to eliminate the concentration of transfected cells around the perimeter of the well, providing for a more even distribution, as could be inferred from the presence of GFP-fluorescence throughout each well.

Example 4

The procedure of Example 1 was repeated, with the following modifications:

Two positive control cell populations were included: (1) cells that were transfected using Lipofectamine 3000 and following the transfection protocol provided by the manufacturer; and (2) dead cells killed by heat shock.

In addition, 1-2 days after sonoporation, cells were stained with a cell membrane integrity dye that positively stains dead cells, i.e., MultiCyt Cell Membrane Integrity Dye Panel FL3 dye (IntelliCyt, Albuquerque, N. Mex.).

Figure 2:
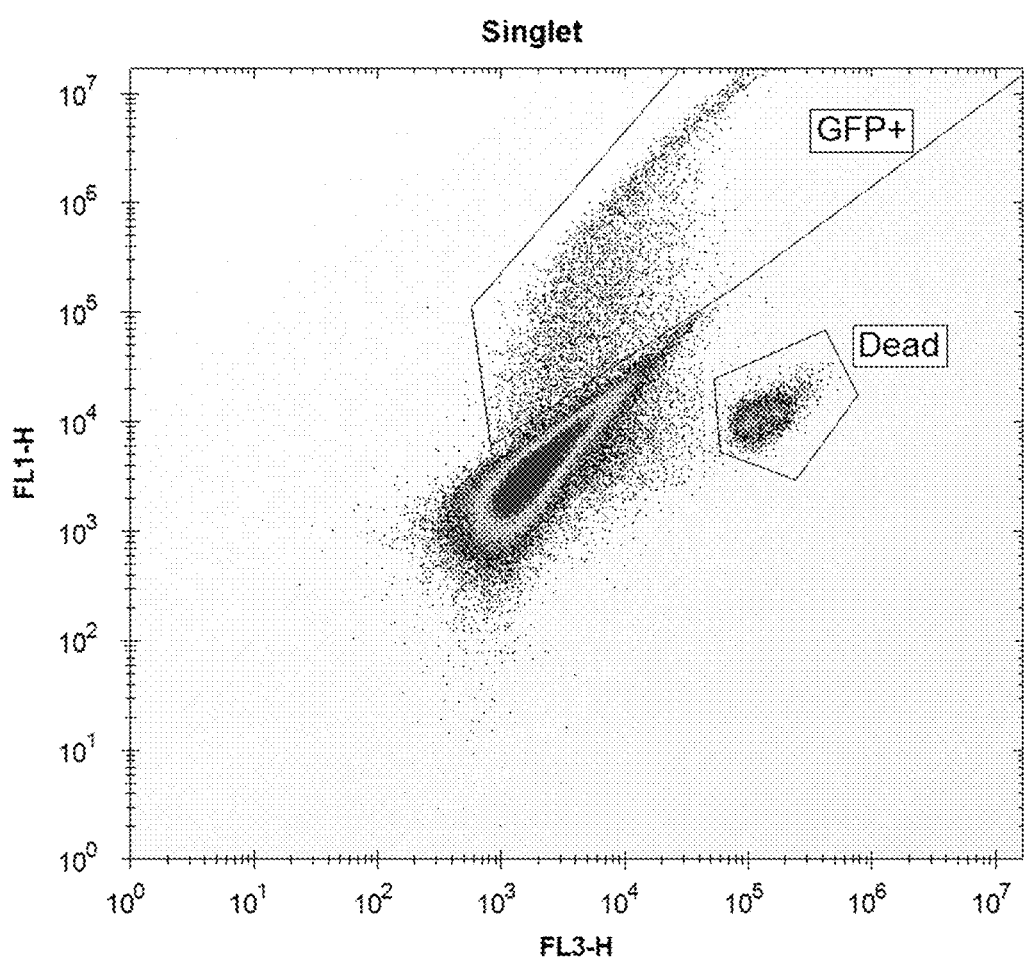
FIG. 2 also derives from the FACS analysis described in Example 4, and indicates that the successfully transfected were detected in the FL1 channel, while dead cells were detected in the FL3 channel.
Figure 3:
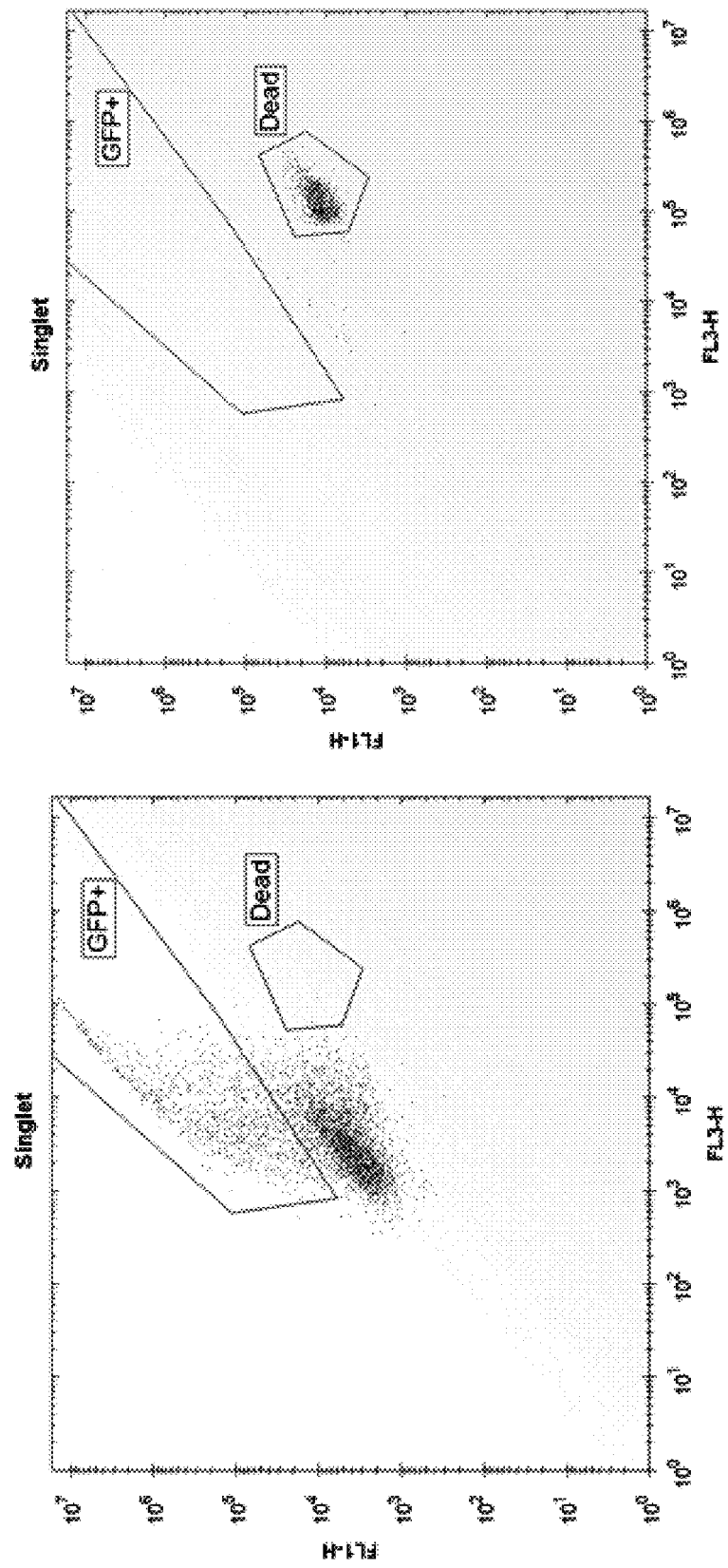
FIG. 3 also derives from the FACS analysis described in Example 4, and separately illustrates the results obtained for the positive controls.
Figure 4:
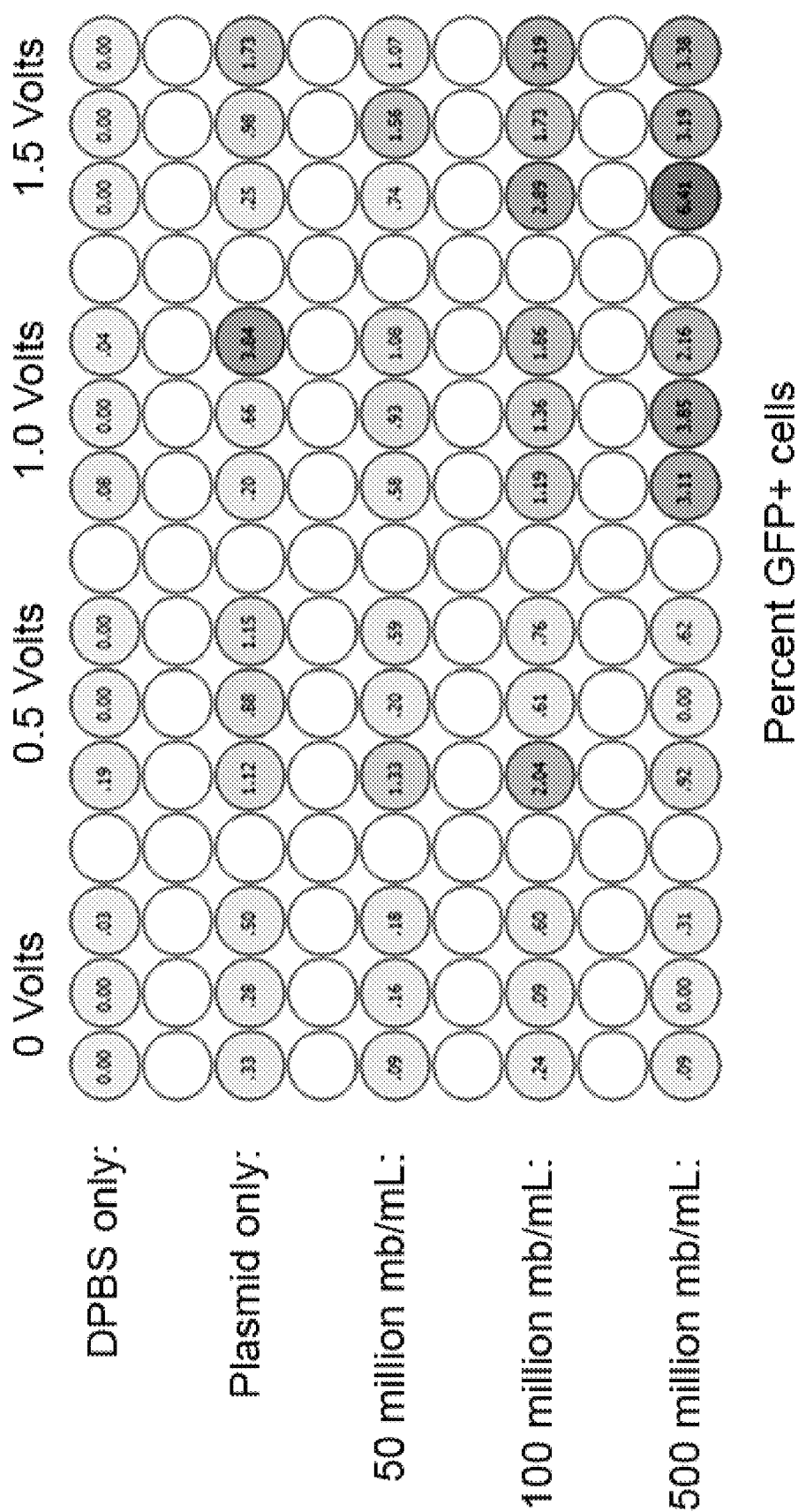
FIG. 4 provides well-by-well results illustrating that the fraction of transfected cells in Example 4 increased with both acoustic power and microbubble concentration.
Figure 5:
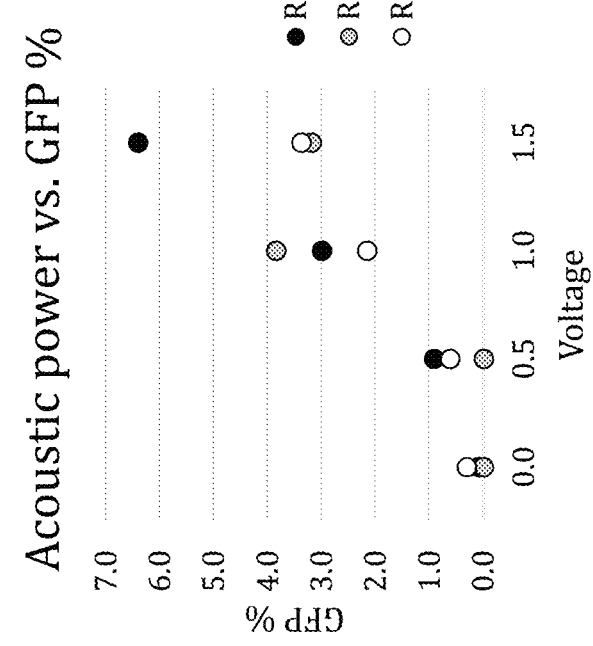
FIG. 5 provides the results in graph form.
Figure 5:
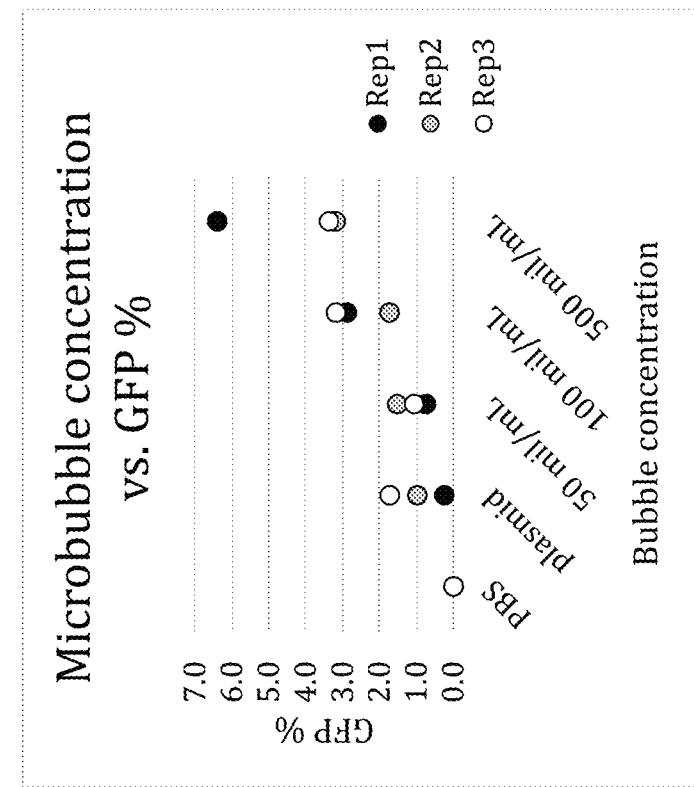
Figure 6:
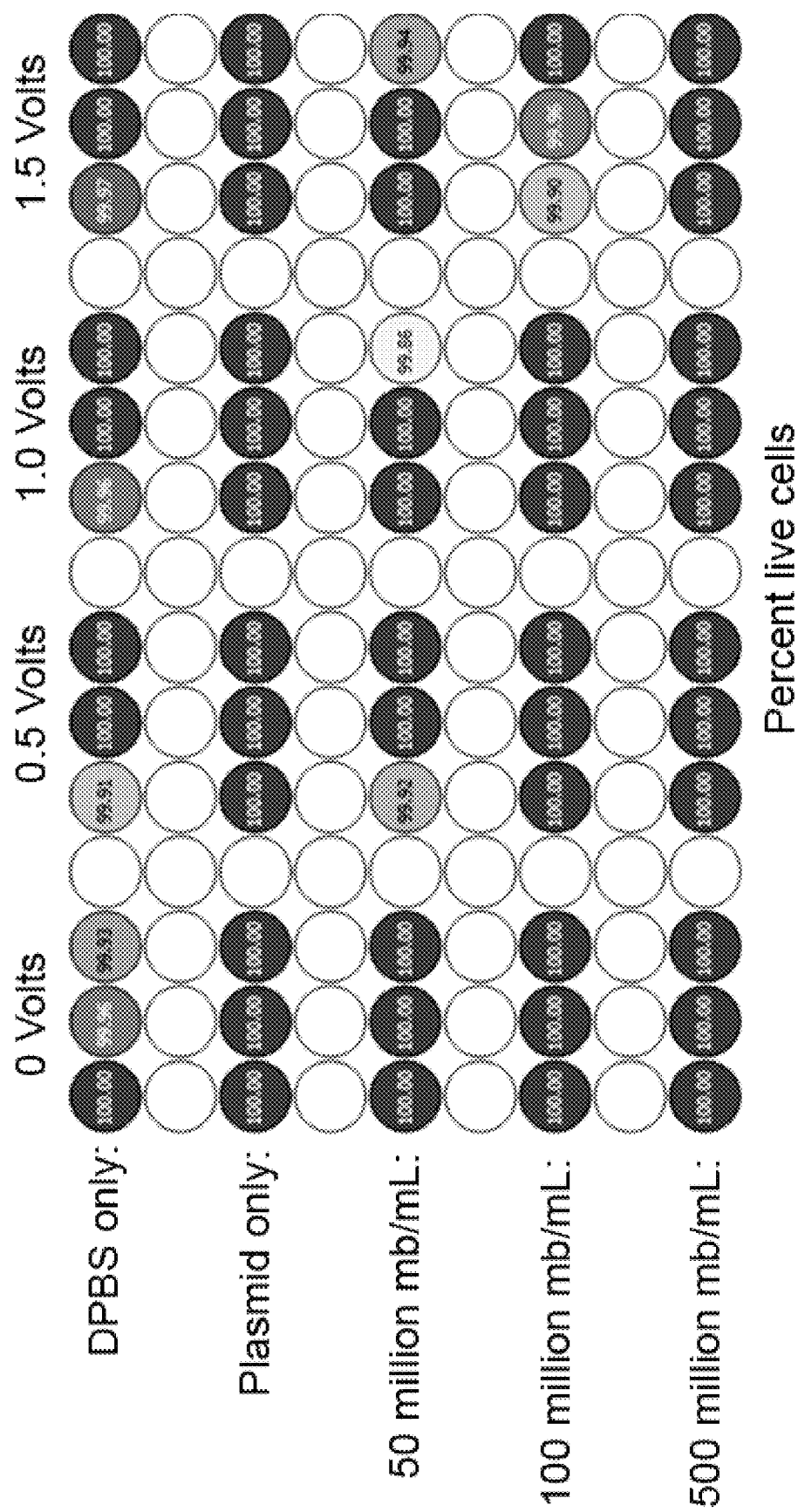
FIG. 6 shows, well by well, that the percentage of live cells remaining post-sonoporation in Example 14 was near 100%, even at the higher voltage used, 1.5 V.
Figure 7:
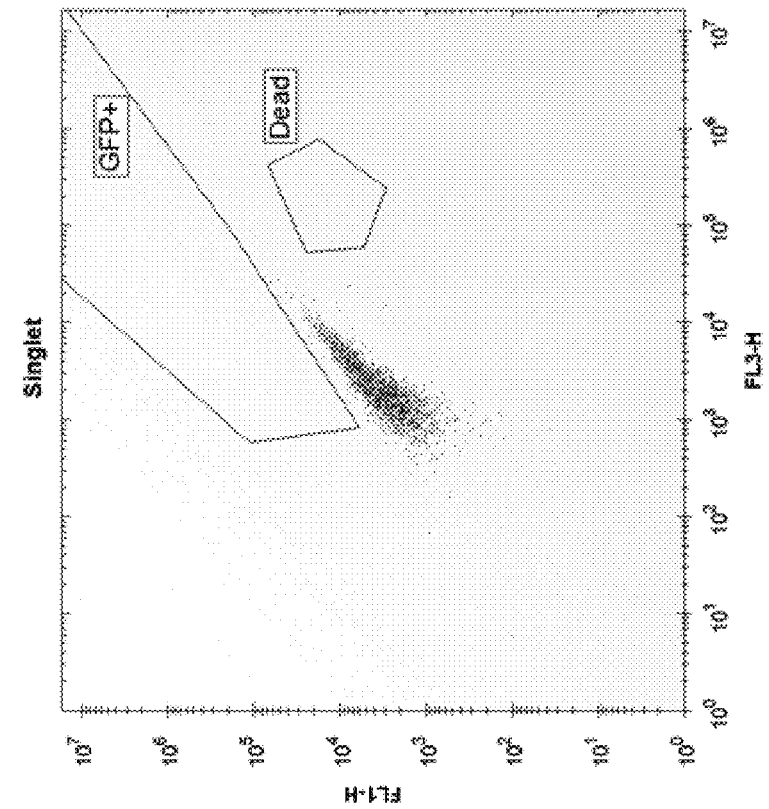
FIG. 7 illustrates the data obtained for the transfected cells and the negative control (i.e., DPBS only, in the absence of microbubbles) in Example 4.
Figure 7:
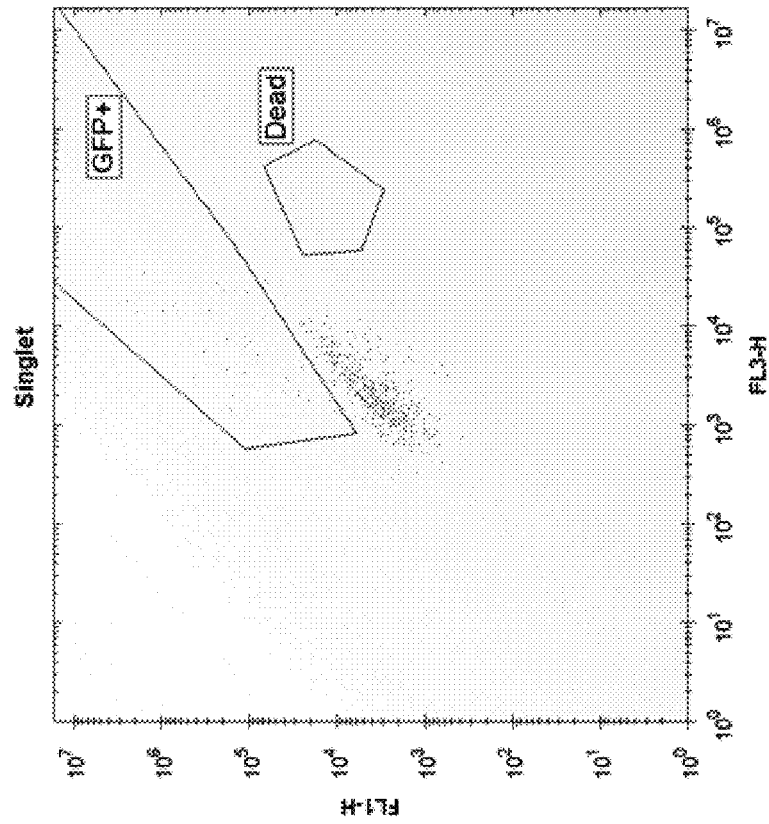

Transfection and survival rates were analyzed using fluorescence-activated cell sorting (FACS); results are provided in FIGS. 1-7. FIG. 1 shows a plot of forward versus side scatter height, enabling differentiation of the HEK-293 cells from microbubbles and other material; dead cells appear as a distinct grouping higher on the SSC-H axis, above the denser cluster of live cells. In FIG. 2, the cells that were transfected with the GFP-encoding plasmid were detected in the FL1 channel, while cells stained with cell membrane integrity dye, i.e., dead cells, were detected in the FL3 channel. The "GFP+" and "dead" labels on the plot were set up manually; these control cell populations are separately illustrated in FIG. 3. As may be concluded from FIG. 4 and FIG. 5, the fraction of host cells that were successfully transfected increased with both acoustic power and microbubble concentration. Also, as indicated in FIG. 6, the percentage of live cells remaining post-transfection is near 100%, even at the highest voltage used, 1.5 V. FIG. 7 illustrates the data obtained for the negative control, i.e., DPBS only, in the absence of microbubbles.

Example 5

This example describes transfection of a CRISPR plasmid using sonoporation. The procedures of the General Protocol and Example 1 were followed, except that a CRISPR plasmid expressing Cas9 and GFP was substituted for the gWiz-GFP plasmid. A 1.5 V sonoporation pulse was used. A dispersion of microbubble-antibody conjugates was prepared in DPBS (as described in the General Protocol), with a concentration of $5 \times 10^8$ microbubble-antibody conjugates per mL of DPBS. This dispersion was then combined with plasmid at the following ratios, given in μg plasmid per μL of dispersion: 1:1; 2:1; 4:1; and 8:1. Three replicates were performed at each ratio. One "no plasmid" negative control row and one "no sonoporation" negative control column were included. As in Example 4, results were assayed using IntelliCyt FACS. GFP positive cells were indicative of CRISPR plasmid uptake, and fluorescent dye stain indicated dead cells.

Figure 8:
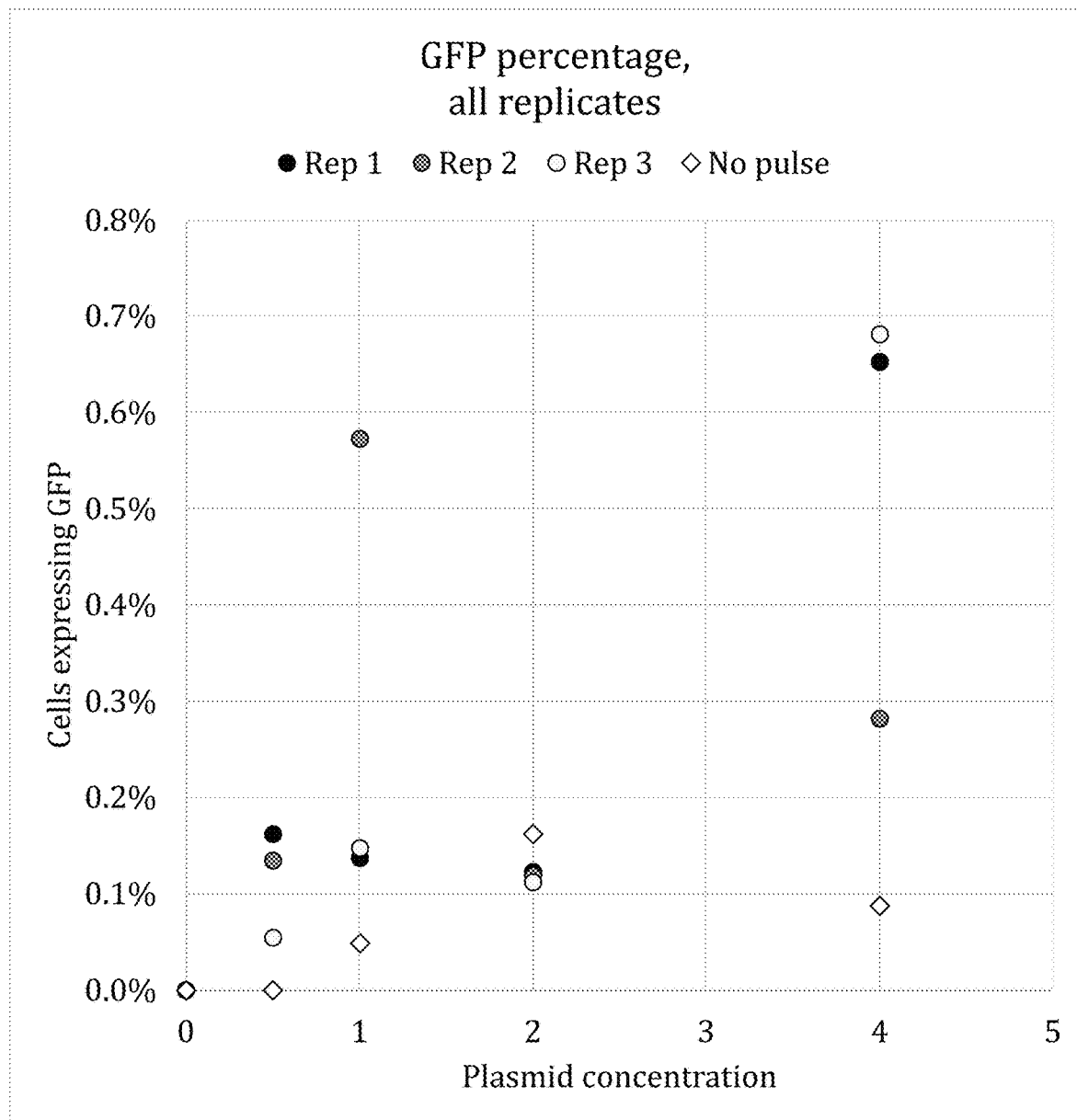
FIG. 8 shows the percentage of GFP-positive cells obtained for each of four plasmid concentrations in the CRISPR transfection experiment described in Example 5.
Figure 9:
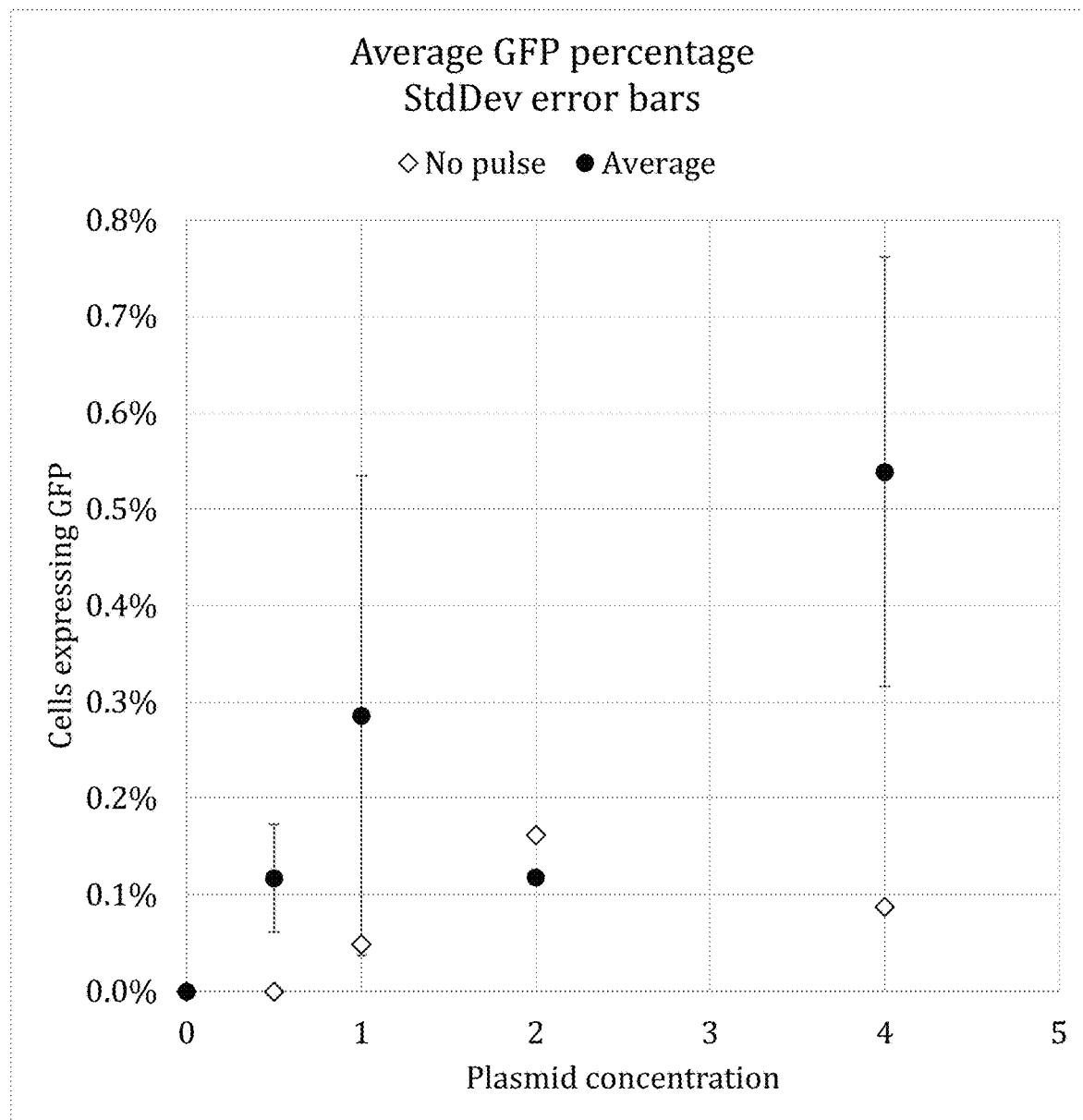
FIG. 9 shows the average percentage of GFP-positive cells at each of four plasmid concentrations, with standard deviation error bars indicated.

The results are shown in FIGS. 8 and 9. FIG. 8 shows the percentage of GFP-positive cells obtained for each of the four plasmid concentrations, and FIG. 9 shows the average percentage of GFP-positive cells at each concentration, with standard deviation error bars indicated. The percentage of GFP-positive cells is above background, indicating that the cells have taken up and are expressing the CRISPR plasmid. The data obtained is also summarized in Table 2:

TABLE 2

| Microbubble-to-cell incubation ratio | Replicate 1 | Replicate 2 | Replicate 3 | No Pulse |
|---|---|---|---|---|
| 0 | 0 | 0 | 0 | 0 |
| 0.5X | 5 | 7 | 2 | 0 |
| 1X | 5 | 21 | 9 | 3 |
| 2X | 4 | 6 | 7 | 10 |
| 4X | 16 | 7 | 24 | 6 |

The singlet cell count data was as follows in Table 3:

TABLE 3

| Microbubble-to-cell incubation ratio | Replicate 1 | Replicate 2 | Replicate 3 | No Pulse |
|---|---|---|---|---|
| 0 | 2363 | 4658 | 3407 | 4185 |
| 0.5X | 3082 | 5199 | 3655 | 5770 |
| 1X | 3640 | 3664 | 6106 | 6129 |
| 2X | 3250 | 5022 | 6247 | 6175 |
| 4X | 2451 | 2479 | 3523 | 6843 |

Figure 10:
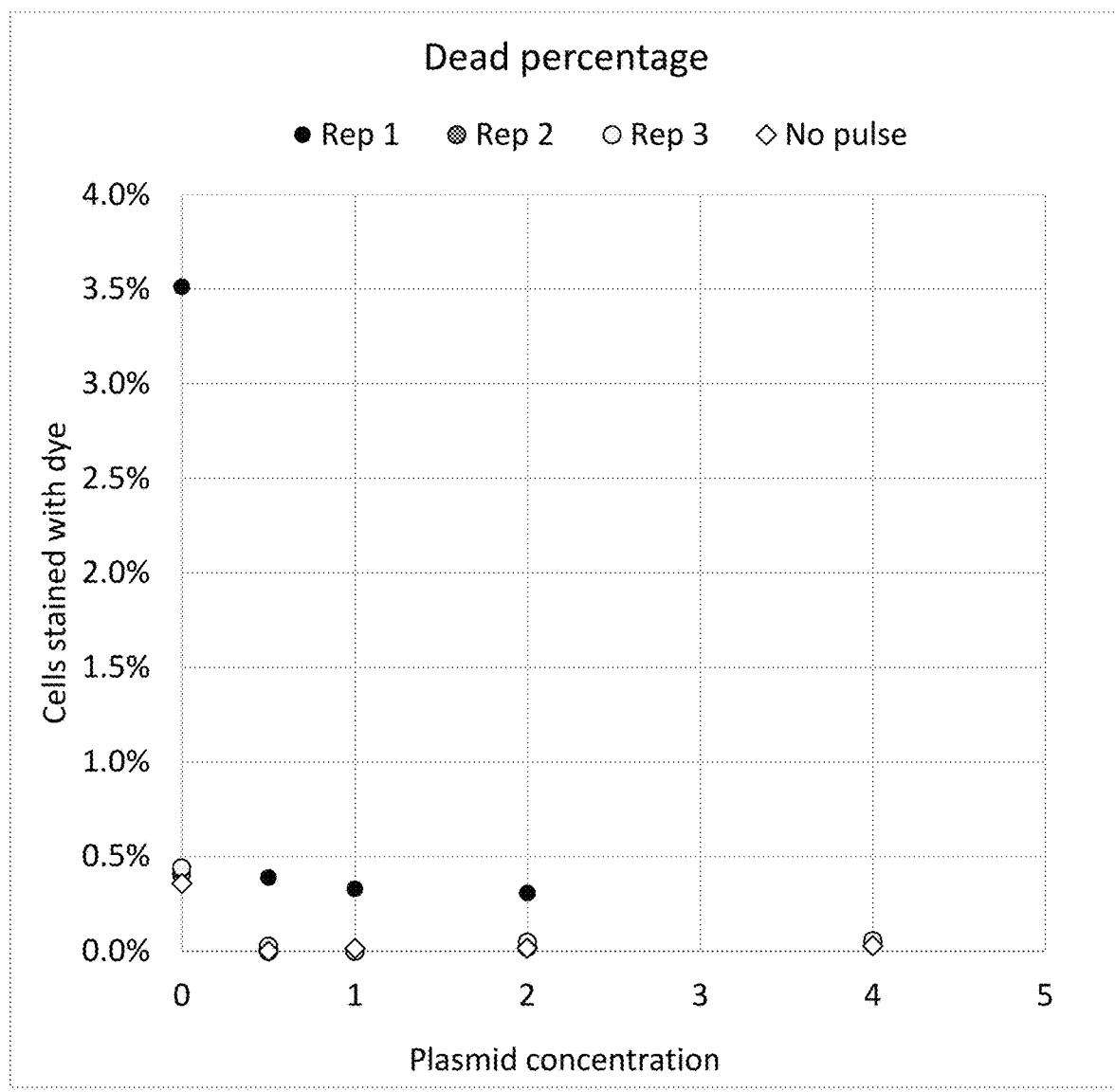
FIG. 10 shows the percentage of dead cells for each of the four plasmid concentrations, as described in Example 5.

The cell death rate after treatment remains low. FIG. 10 shows the percentage of dead cells for each of the four plasmid concentrations. The data obtained is also summarized in Table 4:

TABLE 4

| Microbubble-to-cell incubation ratio | Replicate 1 | Replicate 2 | Replicate 3 | No Pulse |
|---|---|---|---|---|
| 0.5X | 3.51% | 0.41% | 0.44% | 0.36% |
| 1X | 0.39% | 0.00% | 0.03% | 0.00% |
| 2X | 0.33% | 0.00% | 0.00% | 0.02% |
| 4X | 0.31% | 0.02% | 0.05% | 0.02% |

The trend in GFP-positive cell percentage increases with plasmid concentration and is above the background negative control, confirming that CRISPR plasmids can be transfected using sonoporation. An increase in transfection success rate should be possible by using a method that is not plasmid-based, such as, for example, a technique involving the use of sonoporation to introduce ribonucleoproteins into target cells.

Example 6

This example describes transfection of HEK-293 cells with a CRISPR Cas9/guide RNA ribonucleotide (RNP), using the Alt-RTMS.p. Cas9 Nuclease 3NLS obtained from Integrated Technologies, Inc. (IDT, Coralsville, Iowa), and the Alt-R™ CRISPR-Cas9 kit (also obtained from IDT), which includes the Alt-R™ CRISPR-Cas9 HPRT positive control crRNA targeting the HPRT gene, the Alt-R™ CRISPR-Cas9 negative control crRNA, and nuclease-free buffer. A fluorescently labeled tracrRNA for complexing with the crRNA was obtained separately (Alt-R™ CRISPR-Cas9 tracrRNA conjugated to ATTO™550, also from IDT).

(a) Preparation of microbubble/DPBS dispersion: This is a modified version of the method described in the General Protocol for preparation of the microbubble/DPBS dispersion. A vial containing the Targesphere SA microbubble dispersion (concentration $2 \times 10^9$ microbubbles/mL) was gently shaken and inverted end-to-end for 10 seconds, until the mixture appeared uniformly opaque. 50 μL of the Targesphere SA dispersion was extracted and introduced into a new 1.5 mL tube. 950 μL DPBS was added, and the dispersion gently mixed. The mixture was then incubated upright at room temperature for 2 minutes, followed by spinning in a Minifuge® for 2 minutes to separate the microbubbles from the dispersion liquid. Using a syringe needle, the infranatant below the white cake of microbubbles was slowly removed until the volume reached 50 μL.

(b) Conjugation of microbubbles to biotinylated antibody: This is a modified version of the method described in the General Protocol for conjugation of microbubbles to biotinylated antibody. 5 μg anti-CD51 biotinylated antibody (i.e., 10 μL of a 0.5 μg/μL solution) were added to 50 μL of the microbubble/DPBS dispersion, such that the mass/count ratio of anti-CD51 antibody to the Targesphere SA microbubbles was $1:2 \times 10^7$. The vial was incubated at room temperature with gentle agitation for about 20 minutes.

(c) Formation of guide RNA: The crRNA and tracrRNA were suspended in the IDT nuclease-free duplex buffer at 200 μM. The crRNA were combined in a 1:1 equimolar ratio, for a final guide RNA concentration of 100 μM:

TABLE 5

| Component | HPRT gRNA, for 10 reactions | Non-targeting (NT) gRNA, for 5 reactions |
|---|---|---|
| HPRT crRNA (200 μM) | 7 μL | — |
| NT crRNA (200 μM) | — | 4 μL |
| tracrRNA-ATTO 550 (200 μM) | 7 μL | 4 μL |
| | 14 μL | 8 μL |

The mixture was heated at 95° C. for five minutes, and then removed from heat and allowed to cool to room temperature.

(d) Formation of the RNP complex: The Cas9 was combined with the guide RNA to create RNPs as described in the Alt-R™ CRISPR-Cas9 User Guide. Briefly, for each well undergoing sonoporation, the guide RNA (i.e., the crRNA:tracrRNA duplex prepared in the preceding step) were diluted in DPBS, with the Cas9 added last and slowly, at a Cas9: gRNA molar ratio of about 1:1.15. The mixture was then incubated at room temperature for 20 minutes. Concentrations were as follows:

TABLE 6

| Component | Vol. required per reaction | HPRT gRNA, for 10 reactions | NT gRNA, for 5 reactions |
|---|---|---|---|
| DPBS | 2.1 µL | 21 µL | 10.5 µL |
| Conjugated crRNA:tracrRNA (100 µM) | 1.2 µL | 12 µL | 6.0 µL |
| Cas9 nuclease (61 µM) | 1.7 µL | 17 µL | 8.5 µL |
|  | 5.0 µL | 50 µL | 25 µL |

(e) Preparation of loaded microbubbles: The vial containing the antibody-microsphere conjugates ("aCD51 Targespheres") was gently flicked to mix. The antibody-microsphere conjugates were then combined with the RNP prepared in the preceding step, incubated for 20 minutes, and then diluted with DPBS to a final concentration of 4 µM RNP and $5 \times 10^8$ microbubble (mb)/mL:

TABLE 7

| Component | HPRT gRNA, for 4 reactions | HPRT gRNA, no microbubbles, for 4 reactions | NT gRNA, for 4 reactions |
|---|---|---|---|
| aCD51 Targespheres | 25 µL | — | 25 µL |
| RNPs (20 µM) | 20 µL | 20 µL | 20 µL |
| Incubate 20 min. |  |  |  |
| DPBS with Ca/Mg | 55 µL | 80 µL | 55 µL |
| Total volume | 100 µL | 100 µL | 100 µL |

(f) Incubation of the aCD51 Targespheres with HEK-293 cells: Growth media (see the General Protocol) was removed from the HEK-293 cells by pipetting. The aCD51Targespheres (i.e., the antibody-conjugated microbubbles) were pipetted up and down to mix well. 25 µL aCD51Targespheres were then pipetted into each well of a 384-well polypropylene microwell plate coated with a tissue-culture coating. The plate was flipped upside down to facilitate binding of the aCD51 Targespheres to the cells, and placed in a 37° C. incubator for five minutes.

(g) Sonoporation: Using reverse pipetting, 75 µL of pre-warmed complete growth media was added to each well, bringing the total fluid volume per well to 100 µL, with an RNP concentration of 1 µM. Sonoporation was carried out using a 2.25 MHz transducer, a 0.5" aperture diameter, and a one-inch focal length (F-number of 2). The transducer was activated to irradiate each reservoir with 300 tonebursts at a burst repetition rate of about 10 Hz, meaning that the tonebursts were spaced apart by 0.1 sec. Each toneburst consisted of 8 cycles of output, corresponding to a toneburst duration of approximately (8/2.25) 3.5 µs. RF frequency was constant throughout the burst output.

(h) Analysis: The rate of successful CRISPR editing was assessed by measuring the number of indels introduced into the HPRT gene, where an "indel" is a change in DNA sequence caused by the insertion or deletion of nucleotides. This was quantified using a T7 endonuclease I (T7E1) digestion assay, which cleaves double-stranded DNA if the two halves of the helix do not perfectly base pair with each other (i.e. if one half contains an indel). After digestion with T7E1, the DNA either remains intact or is cleaved into two smaller fragments. The digested DNA is analyzed using gel electrophoresis to separate the fragments by size, and the amount of cleaved versus full length fragments was analyzed.

T7 endonuclease I CRISPR indel detection assay: Cells were washed with DPBS and lysed using Epicentre QuickExtract DNA extraction solution. The resulting genomic DNA was PCR amplified using primers flanking the site of interest (i.e., the HPRT gene locus). The PCR products were heated to 95° C. to denature them and then slowly cooled to room temperature, encouraging the formation of mismatched pairs. T7 endonuclease I was then added and incubated at 37° C. for 1 hour, cleaving any double-stranded DNA with a >1 base pair mismatch. The digested DNA was then diluted and run out on the AATI Fragment Analyzer using the CRISPR Discovery Gel Kit to measure percent cleavage.

To measure percent cleavage, the AATI ProSize software compared the amount of "full length" DNA present versus that found in smaller "fragment 1" and "fragment 2" bands. This cleavage percentage is a proxy for the percent editing performed by CRISPR in the cell population. However, the T7E1 enzyme cannot detect 1 base pair indels, which can comprise up to 30% of CRISPR editing events. Thus, the cleavage percentage as measured by this assay is a significant underestimation of the true rate of indel formation.

$$\text{Cleavage \%} = \frac{\text{mean } nmol \text{ in Fragment 1 \& 2}}{nmol \text{ in Full Length} + (\text{mean } nmol \text{ in Fragment 1 \& 2})}$$

The experimental work was repeated and a second set of results generated. The two experiments are referred to below as Run 1 and Run 2.

Figure 11:
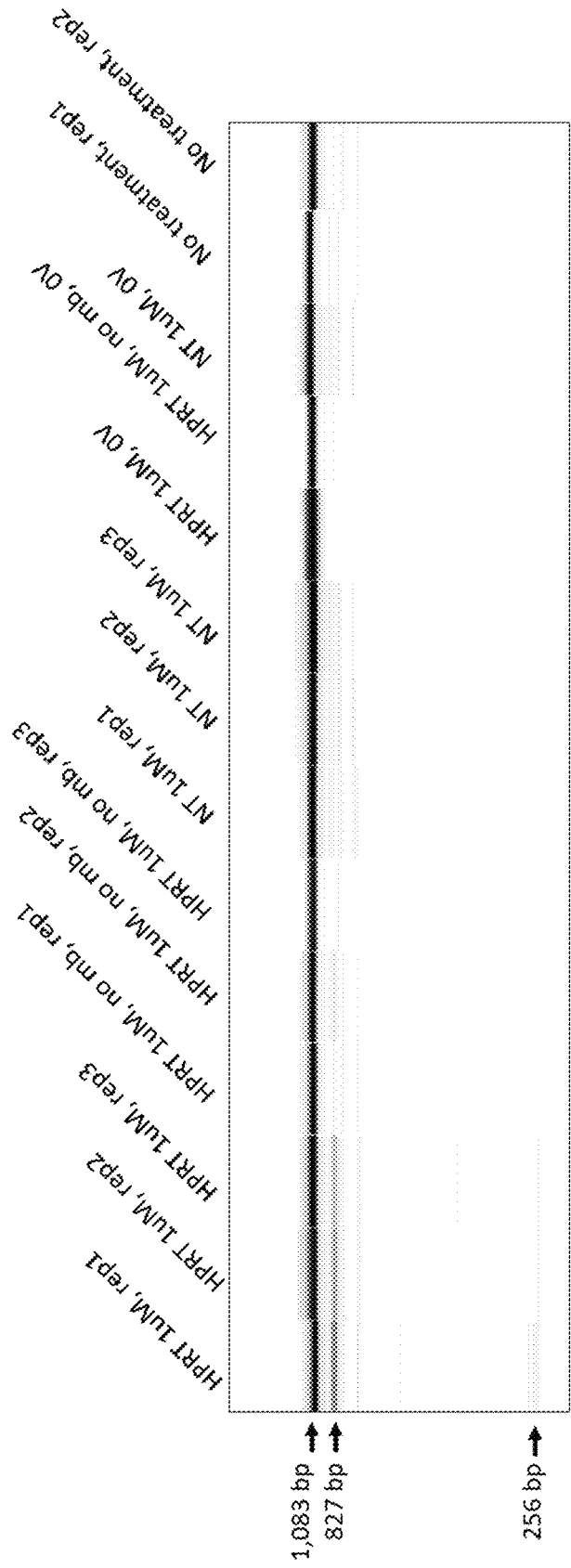
FIG. 11 illustrates the results of the mismatch cleavage assay and analysis for the CRISPR transfection experiment of Example 6, Run 1.
Figure 12:
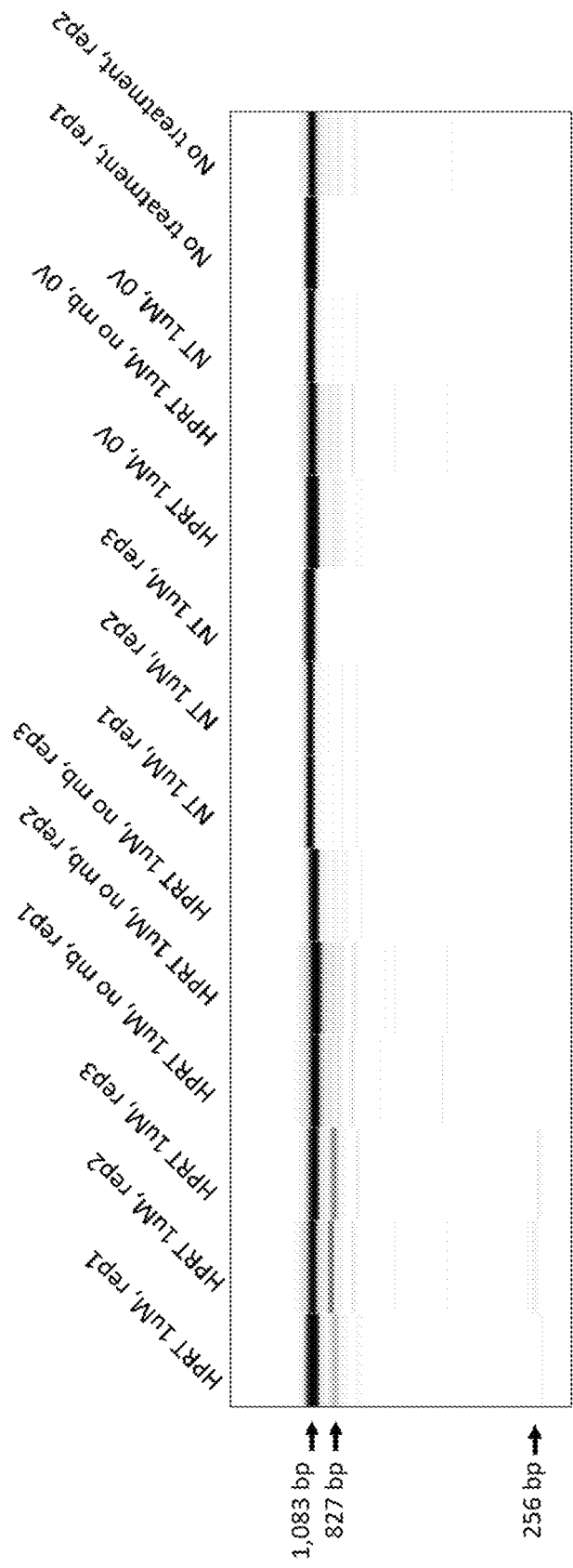
FIG. 12 illustrates the results of the mismatch cleavage assay and analysis for the CRISPR transfection experiment of Example 6, Run 2.

Results: FIG. 11 shows a capillary electrophoresis gel illustrating the results of the mismatch cleavage assay and analysis for Run 1; FIG. 12 is a capillary electrophoresis gel providing the results for Run 2. The 1,083 bp fragment is the full length PCR product, while "fragment 1" is 827 bp and "fragment 2" is 256 bp. Both figures show cleavage in the experimental samples and a lack of cleavage in all controls, indicating that CRISPR transfection and editing was successful. Table 8 gives the percent cleavage for each run:

TABLE 8

| Experiment: |  | Run 1 | Run 2 |
|---|---|---|---|
| HPRT gRNA | HPRT rep1 | 27.50% | 20.18% |
|  | HPRT rep2 | 20.37% | 27.81% |
|  | HPRT rep3 | 17.33% | 24.56% |
| No microbubbles | HPRT no mb, rep1 | 4.69% | 6.21% |
|  | HPRT no mb, rep2 | 8.61% | 6.45% |
|  | HPRT no mb, rep3 | 5.26% | 6.36% |
| Non-targeting gRNA | NT rep1 | 5.05% | 3.98% |
|  | NT rep2 | 4.51% | 4.61% |
|  | NT rep3 | 4.47% | 2.56% |
| No volts | HPRT 0 V | 4.99% | 8.04% |
|  | HPRT no mb, 0 V | 4.79% | 7.92% |
|  | NT 0 V | 4.81% | 3.79% |
| No treatment | No treatment | 4.27% | 2.71% |
|  | No treatment | 4.09% | 5.70% |

Figure 13:
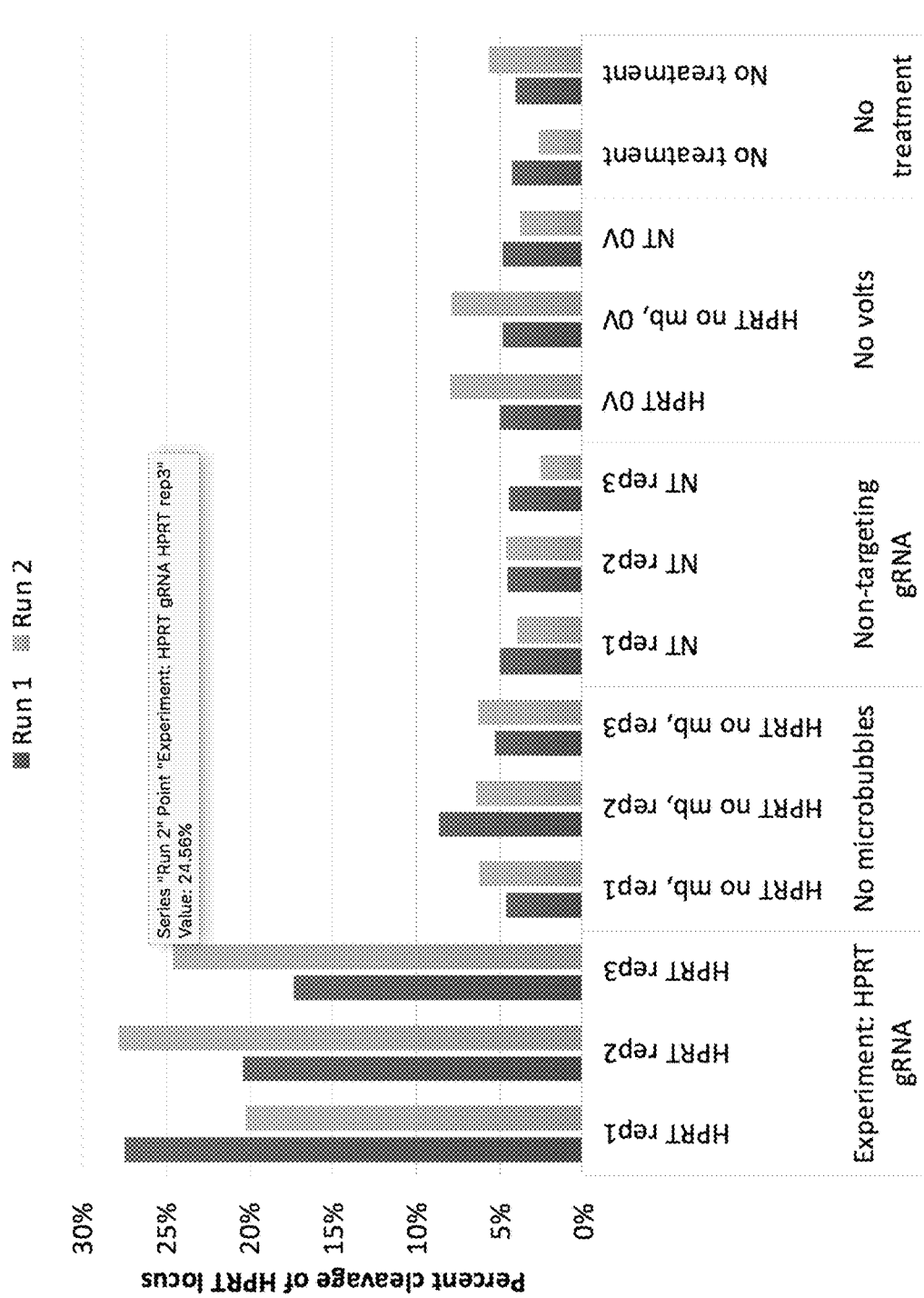
FIG. 13 is a bar graph indicating the percentage cleavage results obtained for Example 6, Runs 1 and 2.

The percentage cleavage results are also illustrated in the bar graph of FIG. 13, in which the darker bars represent the results of Run 1, and the lighter bars represent the results of Run 2.

Figure 14:
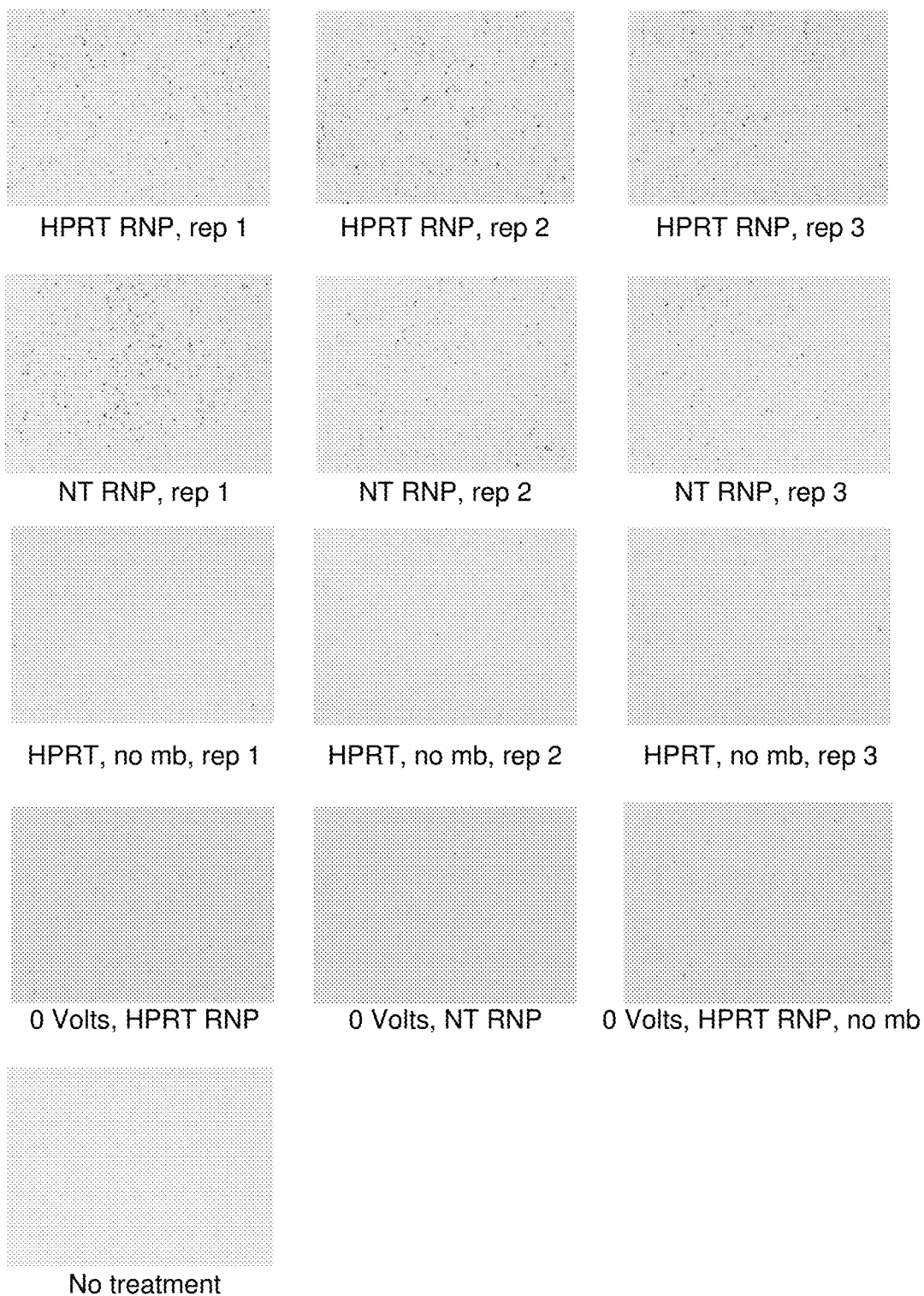
FIG. 14 provides fluorescence images obtained for the transfected host cells in Example 6, Run 2, using an EVOS fluorescent microscope with an RFP light cube to detect the labeled tracrRNA.

FIG. 14 are fluorescence images obtained for Run 2, using an EVOS fluorescent microscope with an RFP light cube to detect the labeled tracrRNA. As can be seen in the images, the HPRT and the non-targeting RNPs successfully transfected into the cells under experimental conditions while the negative control conditions resulted in very low uptake.

We claim:

1. A method for transfecting host cells, comprising contacting, in a reservoir, host cells in a host-cell compatible fluid medium with microbubble-antibody conjugates and an exogenous material to be transfected into the host cells to provide a host cell transfection mixture, and sonoporating the host cell transfection mixture so provided by irradiating the reservoir with acoustic radiation generated by two transducers operating in concert but at different frequencies, wherein one of the transducers comprises an annular transducer operably mounted around and enclosing a standard transducer.

2. The method of claim 1, wherein the annular transducer operates at a frequency in the range of about 1 MHz to about 2.5 MHz.

3. The method of claim 2, wherein the standard transducer operates at a frequency in the range of about 6 MHz to about 20 MHz.

4. The method of claim 1, wherein one of the two transducers primarily functions to supply the acoustic energy for sonoporation and the other transducer delivers acoustic energy to enable acoustic ejection of sonoporated cells from the fluid medium.

5. The method of claim 1, wherein one of the two transducers primarily functions to supply the acoustic energy for sonoporation and the other transducer delivers acoustic energy to change the relative position of the microbubbles with respect to the host cells.

6. The method of claim 5, wherein the relative position of the microbubbles with respect to the host cells does is changed to bring the microbubbles and the host cells in proximity of each other to facilitate sonoporation.

7. The method of claim 4, wherein the microbubbles and the host cells are positioned in proximity of each other in a region of acoustic intensity effective to cause sonoporation.

8. The method of claim 1, wherein the reservoir is contained within a plurality of reservoirs each comprising additional host cells, microbubble-antibody conjugates, an exogenous material to be transfected into the host cells, and a host cell-compatible fluid medium.

9. The method of claim 8, further comprising repeating the method for the additional reservoirs to transfect the additional host cells therein.

10. The method of claim 9, wherein the method is repeated with a reservoir-to-reservoir transition time of at most about 0.5 seconds.

11. The method of claim 10, wherein the reservoir-to-reservoir transition time is at most about 0.1 seconds.

12. The method of claim 11, wherein the reservoir-to-reservoir transition time is at most about 0.001 seconds.

13. The method of claim 8, wherein the plurality of reservoirs comprises 96 reservoirs, 384 reservoirs, 1536 reservoirs, 3456 reservoirs, or more than 3456 reservoirs.

14. The method of claim 13, wherein the reservoirs are arranged in an array.

15. The method of claim 14, wherein the reservoirs are contained within a substrate comprising an integrated multiple reservoir unit.

16. The method of claim 15, wherein the integrated multiple reservoir unit comprises a well plate.

* * * * *